(12) United States Patent
Wold

(10) Patent No.: US 9,641,680 B1
(45) Date of Patent: May 2, 2017

(54) CROSS-LINKING CALL METADATA

(71) Applicant: Eric Wold, American Fork, UT (US)

(72) Inventor: Eric Wold, American Fork, UT (US)

(*) Notice: Subject to any disclaimer, the term of this patent is extended or adjusted under 35 U.S.C. 154(b) by 0 days.

(21) Appl. No.: 15/134,265

(22) Filed: Apr. 20, 2016

Related U.S. Application Data

(60) Provisional application No. 62/150,803, filed on Apr. 21, 2015, provisional application No. 62/156,755, filed on May 4, 2015.

(51) Int. Cl.
| | | |
|---|---|---|
| H04M 1/64 | (2006.01) |
| H04M 3/51 | (2006.01) |
| H04M 3/42 | (2006.01) |
| H04W 84/04 | (2009.01) |
| A61B 5/16 | (2006.01) |
| H04W 84/12 | (2009.01) |

(52) U.S. Cl.
CPC ......... *H04M 3/5141* (2013.01); *A61B 5/167* (2013.01); *H04M 3/42221* (2013.01); *H04M 3/5175* (2013.01); *H04W 84/042* (2013.01); H04M 2201/405 (2013.01); H04M 2203/556 (2013.01); H04W 84/12 (2013.01)

(58) Field of Classification Search
CPC .................................................. H04M 3/5141
See application file for complete search history.

(56) References Cited

U.S. PATENT DOCUMENTS

| | | | |
|---|---|---|---|
| 6,327,345 B1 | 12/2001 | Jordan |
| 6,427,137 B2 | 7/2002 | Petrushin |
| 6,757,361 B2 | 6/2004 | Blair et al. |
| 8,094,803 B2 | 1/2012 | Danson et al. |
| 8,150,692 B2 | 4/2012 | Stewart et al. |

(Continued)

FOREIGN PATENT DOCUMENTS

| | | |
|---|---|---|
| CN | 103685613 A | 3/2014 |
| EP | 2437477 A1 | 4/2012 |

(Continued)

OTHER PUBLICATIONS

Brown, Troy E et al., "Ability of the Vericator to Detect Sumggler at a Mock Security Checkpoint," DoD Polygraph Institute Research Division, 74 pgs., Feb. 24, 2003.

(Continued)

*Primary Examiner* — Joseph T Phan
(74) *Attorney, Agent, or Firm* — Lowenstein Sandler LLP

(57) ABSTRACT

Methods, systems, and devices for cross-linking events and persons using anonymized voice fingerprint identifiers (IDs) and call metadata are described. The method can include retrieving, form a centralized database, call metadata associated with a caller index ID. The method can include determining call metadata characteristics for the call metadata. The method can include matching the call metadata characteristics of the call metadata with characteristics associated with a personality type of a psychological behavioral model. The method can include generating a caller profile that comprises personality type information for the personality type. The method can include associating the caller profile with the caller index ID. The method can include storing the caller profile in an entry in the centralized database associated with the caller index ID.

20 Claims, 14 Drawing Sheets

(56) References Cited

U.S. PATENT DOCUMENTS

| | | | |
|---|---|---|---|
| 8,359,219 B2* | 1/2013 | Chishti | H04M 3/5232 |
| | | | 705/7.13 |
| 8,594,285 B2 | 11/2013 | Conway et al. | |
| 8,718,262 B2 | 5/2014 | Conway et al. | |
| 8,719,035 B2 | 5/2014 | Stewart et al. | |
| 8,793,131 B2 | 7/2014 | Guerra et al. | |
| 8,837,687 B2 | 9/2014 | Odinak et al. | |
| 8,837,706 B2 | 9/2014 | Odinak et al. | |
| 8,983,054 B2 | 3/2015 | Conway et al. | |
| 9,401,989 B2* | 7/2016 | Uba | H04M 3/5175 |
| 9,444,940 B2* | 9/2016 | Skiba | H04M 3/5233 |
| 9,456,086 B1* | 9/2016 | Wu | H04M 3/5233 |
| 9,501,551 B1* | 11/2016 | Weissgerber | G06F 17/30707 |
| 2004/0101127 A1* | 5/2004 | Dezonno | H04M 3/523 |
| | | | 379/265.02 |
| 2010/0241430 A1 | 9/2010 | Bacchiani et al. | |
| 2012/0253805 A1 | 10/2012 | Rajakumar et al. | |
| 2013/0006874 A1 | 1/2013 | Klemm | |
| 2014/0136194 A1 | 5/2014 | Warford et al. | |
| 2014/0188730 A1 | 7/2014 | Murgai et al. | |
| 2014/0244260 A1 | 8/2014 | Stewart et al. | |
| 2014/0330563 A1 | 11/2014 | Faians et al. | |
| 2015/0055763 A1 | 2/2015 | Guerra et al. | |

FOREIGN PATENT DOCUMENTS

| | | |
|---|---|---|
| TW | M448095 U1 | 3/2013 |
| WO | 0046720 A2 | 8/2000 |

OTHER PUBLICATIONS

Eriksson, Anders, "Tutorial on Forensic Speech Science," Department of Linguistics, Gothenburg University, 14 pgs., 2005.

International Search Report and Written Opinion received for International Patent Application No. PCT/US2016/028641, mailed Jul. 21, 2016, 11 pages.

* cited by examiner

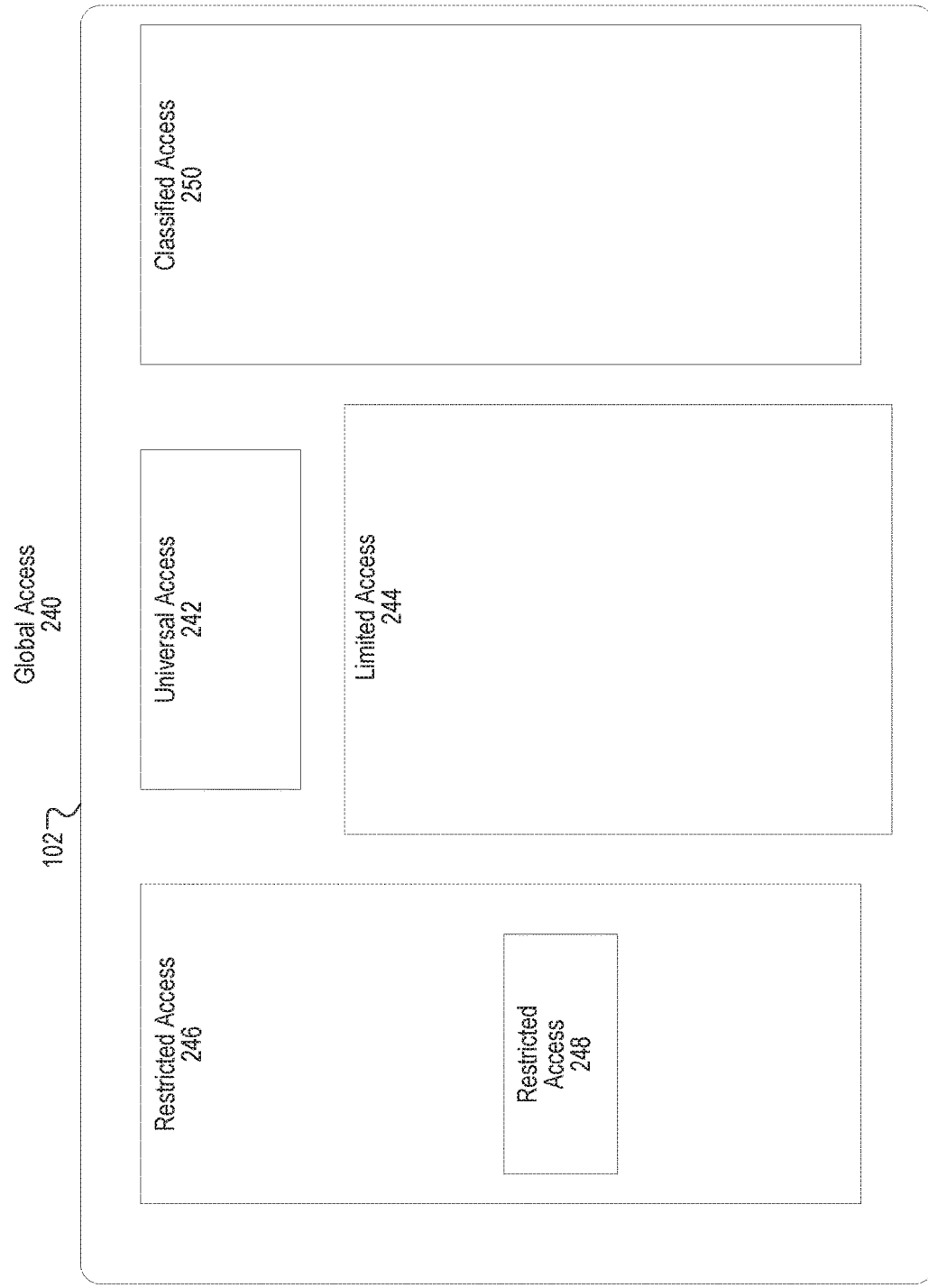

CROSS-LINKING CALL METADATA

RELATED APPLICATION

This application claims the benefit of U.S. Provisional Application No. 62/150,803, filed Apr. 21, 2015 and U.S. Provisional Application No. 62/156,755, filed May 4, 2015, the entire disclosures of which is incorporated herein by this reference.

BACKGROUND

A call centers can be used to facilitate a receipt, response, and routing of incoming calls relating to customer service, retention, and sales. Typically, a customer may be connected with a customer service representative ("CSR") who may be responsible for answering the customer's inquiries and/or directing the customer to an appropriate individual, department, information source, or service based on a customer's needs. While some companies have in-house call centers to handle customer calls, in many cases a company may hire a third party call center to handle the customer calls.

The third party call center may handle calls for multiple departments of a company and/or for multiple companies. Traditionally, each time a customer calls a CSR can be assigned to the call, often times the assigned CSR may be different for different calls from a same customer. For example, a customer may make a first call to the call center and be assigned to a first CSR and when the customer makes a second call to the call center the customer can be assigned to a second CSR. Additionally, the customer may be directed to a first call center when they call regarding a first service and may be directed to a second call center when they call regarding a second service.

A customer call may be monitored and/or recorded and the call may be analyzed to determine a customer's needs. For example, the calls can be monitored so a supervisor of the CSR can ensure quality service may be provided by the CSR to the customer. However, as different calls by a customer may be directed to different call centers, each call may be treated as an isolated event. Treating the call as an isolated event may limits a CSR's ability to understand and engage a customer.

BRIEF DESCRIPTION OF DRAWINGS

The present invention will be understood more fully from the detailed description given below and from the accompanying drawings of various embodiments of the present invention, which, however, should not be taken to limit the present invention to the specific embodiments, but are for explanation and understanding only.

FIG. 2B illustrates the centralized database with different access layers according to one embodiment.

DETAILED DESCRIPTION

Individuals may place calls into a variety of different call agents. For example, an individual may call a call center for a product issue, a company to inquire about a service they offer, and a government entity to discuss a regulatory issue. A call agent can be a call center, a customer service hotline, an individual, a customer help hotline, a division or department within a company, a government entity, or other individuals or entities that receive calls on behalf of an individual or entity. For example, many companies have call centers to provide customer relation services, such as customer service, customer retention, and sales. When a customer calls a call center, the call can be directed to a call agent, such as a customer service representative ("CSR"), who will service the call.

The call center may handle calls for multiple departments of a company and/or for multiple companies. Traditionally, each time a customer's call is directed to a call center, a CSR can be assigned to the call. The CSR assigned to the call may be different for different calls by the same customer. In one example, the CSR may be randomly assigned to the call. In another example, a call directing service may not identify that the current call is for the same customer as a previous call. The different CSRs provide inconsistent service, as the CSRs have no history or baseline for the customer to aid the CSR to understand a caller's disposition or temperament.

The embodiments described herein may address the above noted deficiency by a customer relationship management ("CRM") device collecting and analyzing call metadata from calls placed one or more caller to call agents. The CRM device can use the call metadata to determine profile information for the caller. The profile information can include the caller's behavioral patterns, personality, disposition, temperament, and so forth. The CRM device can aggregate and cross-link events and customer interactions across different call. The CRM device can cross-link calls from the caller to different call agents, such as calls to different call centers or companies. The CRM device can cross-link calls from the caller for different products or services. One advantage of the CRM device aggregating and cross-linking events can be to improving a quality of a call agent's interaction with a caller by providing the call agent's with a user profile of the caller. For example, CRM device can provide a CSR with a behavioral or personality baseline for the caller so that the CSR can detect a variance or deviation in the caller's behavior.

Figure 1:
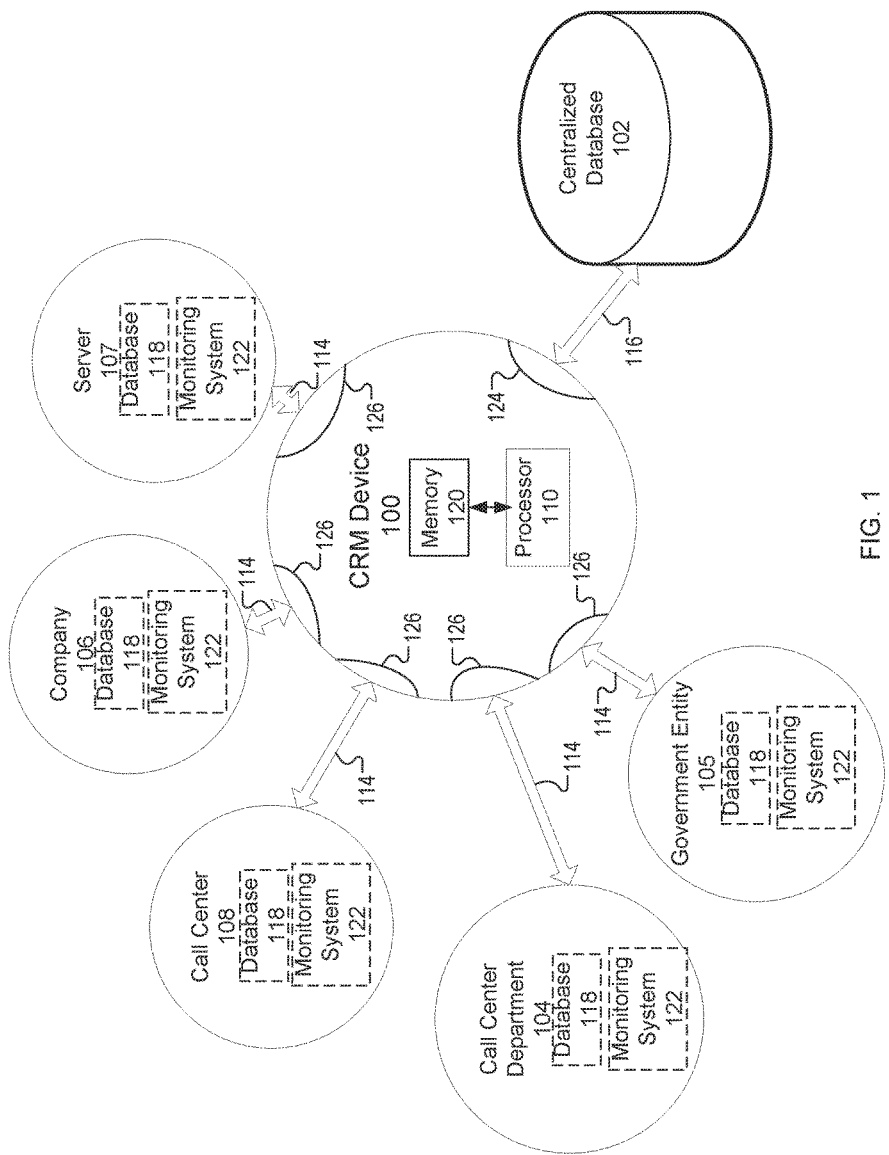
FIG. 1 illustrates a CRM device with a processing device to aggregate customer information from a variety of call agents according to one embodiment.

FIG. 1 illustrates a CRM device 100 with a processor 110 to aggregate customer information from a variety of call agents 104-108 according to one embodiment. The CRM device 100 can be an electronic device, such as a server, a desktop computer, a smart phone, a personal digital assistant (PDA), a tablet computer, a netbook, a laptop, and the like. The CRM device 100 can include a database interconnect 124 to communicate with a centralized database 102. The can include one or more network interfaces 126 to communicate with a system or device of the call agents 104-108.

The call agents 104-108 can include call center departments 104, government entities 105, companies 106, servers 107, and/or the call center 108. The listed example of call agents is not intended to be limiting, but rather to provide examples of different call agents. The CRM device 100 can communicate with a system or device of the call agents 104-108 via one or more first network connections 114 between the call agents 104-108 and the network interfaces 126. The systems and devices of the call agents 104-108 can include call monitoring systems 122, databases 118, communication systems for audio and/or video communications (such as telephonic communications, and so forth.

The call agents 104-108 can be located at different locations. For example, a call center 108 may be located in the state of Utah in the United States of America and a company 106 can be located in Beijing, China. The call monitoring systems 122 of the call agents 104-108 can monitor and record call metadata for calls received from callers. The calls can be digital signals that represent audio and/or video communications between individuals, e.g., telephone calls.

In one example, the call metadata can include audio and/or video recordings of the call. In another example, the call metadata can include identifying information received during the call. In one example, the identifying information received from a CSR via an input device during the call, as discussed in greater detail in the proceeding paragraphs. In another example, the identifying information can be information generated by the processor 110, the call monitoring systems 122, or a processing device of a call agent 104-108 that is using a voice recognition system. The identifying information can include personal information about a caller, such as their gender, age, name, a customer's name, a customer's address, a customer's social security information, and so forth.

In one example, the call monitoring systems 122 can record the call metadata into databases 118. In one example, the databases 118 can be internal to the call agents 104-108, such as on-site servers or memories. In another example, the databases 118 can be communicatively coupled to the call monitoring systems 122 can be located at a different location than the call monitoring systems 122. The CRM device 100 can access and retrieve call metadata from the databases 118 and store the call metadata at the centralized database 102. References herein to the CRM device 100 communicating with the call agents 104-108 can be the CRM device 100 communicating with the call monitoring systems 122 of the call agents 104-108, the databases 118, or other processing devices used by the call agents 104-108 to communicate with a caller and record call metadata.

The CRM device 100 or the processor 110 of the CRM device 100 can communicate with the centralized database 102 via a second network connection 116 using the database interconnect 124. In one embodiment, the CRM device 100 can include a wired communication port to establish the first network connection 114 and/or the second network connection 116 via a wired communication channel to communicate data, such as a communication channel via an Ethernet cable or a coaxial cable. In another embodiment, the CRM device 100 can include an antenna to establish the first network connection 114 and/or the second network connection 116 via a wireless communication channel to communicate data, such as a cellular communication channel or a wireless local area network (WLAN) communication channel.

The antenna described herein can be used for wide area network (WAN) technologies, such as cellular technologies including Long Term Evolution (LTE®) frequency bands, third generation (3G) frequency bands, Wi-Fi® frequency bands or other wireless local area network (WLAN) frequency bands, Bluetooth® frequency bands or other personal area network (PAN) frequency bands, global navigation satellite system (GNSS) frequency bands (e.g., positioning system (GPS) frequency bands), and so forth. In one example, the LTE® frequency bands can include a B1 band, a B2 band, a B4 band, a B5 band, a B8 band, a B12 band, or a B17 band.

In another example, the cellular network may employ a third generation partnership project (3GPP®) release 8, 9, 10, 11, or 12 or Institute of Electronics and Electrical Engineers (IEEE®) 802.16p, 802.16n, 802.16m-2011, 802.16h-2010, 802.16j-2009, 802.16-2009. In another example, the wireless network may employ the WI-FI® technology following IEEE® 802.11 standards defined by the WI-FI ALLIANCE® such as the IEEE® 802.11-2012, IEEE® 802.11ac, or IEEE® 802.11ad standards. In another example, the electronic device may use the antenna structure to communicate with other devices using a secure WLAN, secure PAN, or a Private WAN (PWAN). Similarly, the electronic device may use the antenna structure to communicate using a BLUETOOTH® technology and IEEE® 802.15 standards defined by the BLUETOOTH® Special Interest Group, such as BLUETOOTH® v1.0, BLUETOOTH® v2.0, BLUETOOTH® v3.0, or BLUETOOTH® v4.0 (including BLUETOOTH® low energy). In another embodiment, the electronic device may use the antenna structure to communicate using a ZIGBEE® connection developed by the ZIGBEE® Alliance such as IEEE® 802.15.4-2003 (ZIGBEE® 2003), IEEE® 802.15.4-2006 (ZIGBEE® 2006), IEEE® 802.15.4-2007 (ZIGBEE® Pro). The preceding frequency bands are not intended to be limiting. The communication device 112 can use the antenna to communicate on other frequency bands, such as GNSS frequency bands (e.g., GPS frequency bands), and so forth.

The CRM device 100 can access the databases 118 of the call agents via the network connections 114. The CRM device 100 can aggregate call metadata from databases 118 to a centralized database 102. In one embodiment, when aggregating the call metadata, the CRM device 100 can filter the call metadata from the databases 118 to remove irrelevant or unnecessary information. In another embodiment, the call metadata in the different databases 118 of the call agents 104-108 can have different formats. When aggregating the call metadata, the CRM device 100 can format the call metadata from the databases 118 to create a common format. For example, the CRM device 100 can format call metadata from the databases 118 in a common order so that fields in entries in the centralized database 102 can have the same order. For example, the call metadata may include CRM data or past call data from prior events found for an individual when the call center has determined the identity of the individual and the individual's information is in the database 118 of the call center. In one example, call metadata from a call center can include relevant metadata (such as region or company info and a caller ID phone number) as well as irrelevant metadata such as (the internet protocol address of a computer used by the CRM). The CRM device can have a common format for the call metadata from the different databases 118 that includes data fields for In one embodiment, the centralized database 102 can be a virtual database where the CRM device 100 can have authorization to access the databases 118 and can access the databases 118 on-demand. For example, the CRM device 100 may be able to search or query the databases 118 as requested by the processor 110 (e.g., on-demand or real-time access to the databases 118). In another embodiment, the centralized database 102 can be communicatively coupled of the CRM device 100. For example, the centralized database 102 can be a server located at a different location than the CRM device 100 and the CRM device 100 can access the centralized database 102 via the network connection 116. In another embodiment, the centralized database 102 can be integrated into the CRM device 100. In another embodiment, the centralized database 102 can be cloud storage.

In one embodiment, the memory 120 can store instructions for the processor 110 to execute. In one embodiment, the memory 120 can integrated into the CRM device 100. In another example, the memory 120 can be coupled to the CRM device 100. The memory can be a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, or any type of media suitable for storing electronic instructions.

The processor 110 can access the call metadata stored at the centralized database 102. In one embodiment, the processor 110 can analyze the call metadata stored at the centralized database 102 to identify a caller. In another example, the processor 110 can analyze the call metadata to determine caller profile for the caller.

Figure 2A:
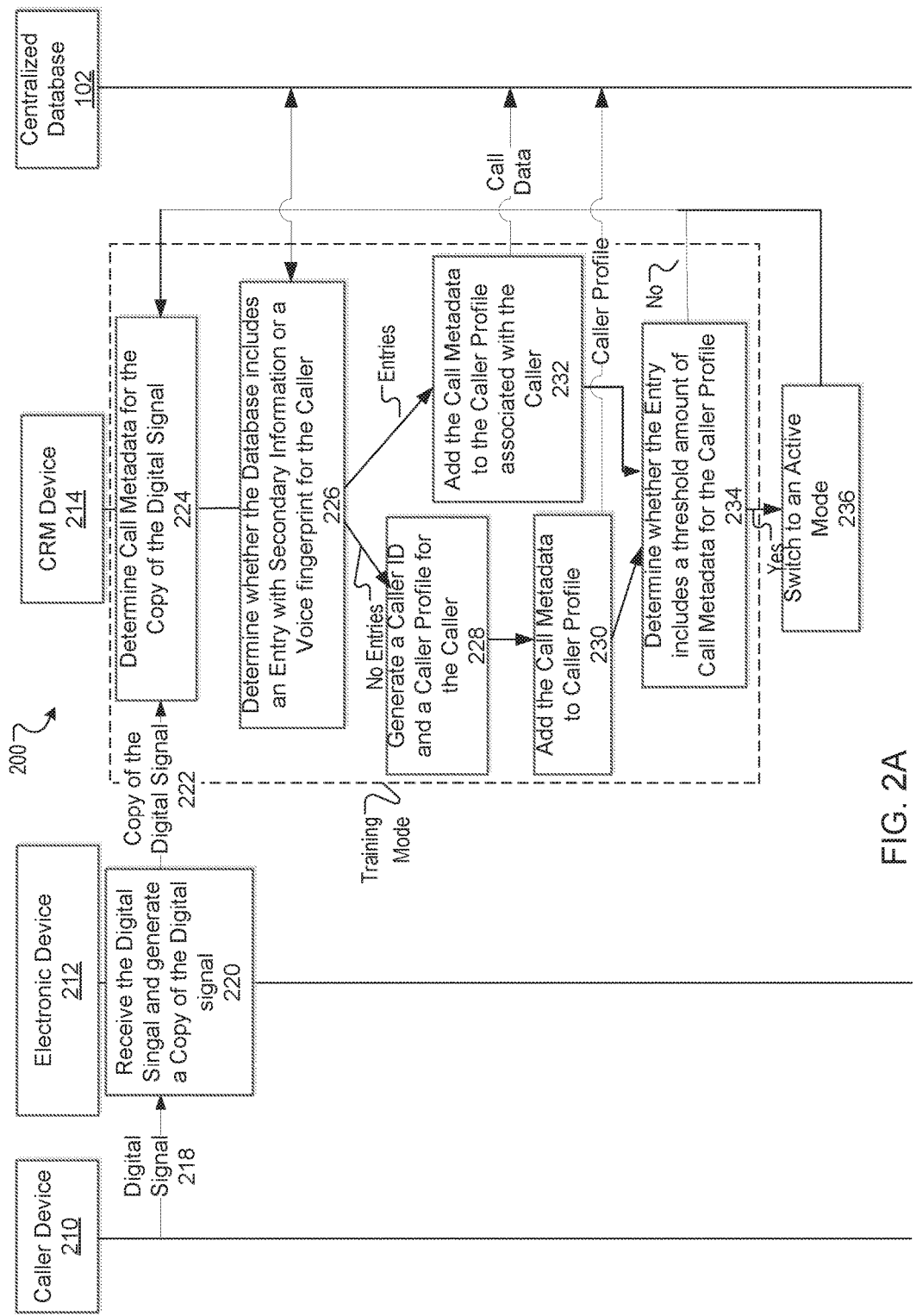
FIG. 2A illustrates a diagram of a method for associating call metadata with a caller according to one embodiment.

FIG. 2A illustrates a diagram of a method 200 for associating call metadata with a caller according to one embodiment. The method 200 may at least partially be performed by processing logic that includes hardware (e.g., circuitry, dedicated logic, programmable logic, microcode, etc.), software (e.g., instructions executed by a processing device), firmware or a combination thereof. The method 200 may be performed by all or part of the CRM device 100 of FIG. 1. For example, the method 200 may be performed by all or part of the processor 110 (FIG. 1) or the communication device 112 (FIG. 1). Some numbers in FIG. 2A are similar to some numbers in FIG. 1 as noted by similar reference numbers unless expressly described otherwise.

Referring to FIG. 2A, the method 200 begins with a caller device 210 placing a call to an electronic device 212 (218). The electronic device can be a communication system for telephonic communications, audio communications, video communications, and so forth. For example the electronic device can be a telephone or a computer system to receive calls from a caller. The call can be a digital signal representing a telephone call, a video call, a conference call, or other communications between to electronic devices. The electronic device 212 can be a telephone, a tablet, a desktop computer, a personal digital assistant (PDA), a smart phone, a voice over internet protocol (VoIP) device, or other electronic device capable of communicating with another device. The method can include the electronic device 212 receiving the digital signal from the caller device 210 and generating a copy of the digital signal (220). For example, the electronic device 212 can be communicate with the caller device 210, such as a telephone call between two telephones, and the electronic device 212 can copy the call and send it to the CRM device 214 for analysis, as discussed in greater detail in the proceeding paragraphs.

The method can include the electronic device 212 sending the copy of the digital signal to the CRM device 214 (222). In one embodiment, the copy of the digital signal can be sent to the CRM device 214 at the same time the caller device 210 and the electronic device 212 are communicating, e.g., relaying of the digital signal. In another embodiment, there may be a lag or delay between the caller device 210 and the electronic device 212 communicating, and the electronic device 212 sending the call metadata to the CRM device 214. The method can include the CRM device 214 determining call metadata for call metadata of the copy of the digital signal (224). The method can include the CRM device 214 generating call metadata In one embodiment, the call metadata characteristics can be call quality information, such as a volume level of the call, an audio and/or video quality level of the call, a length of time of the call, and so forth. In another embodiment, the call metadata characteristics can be call content, including key words used during the call, a speed of speech of the caller or receiver, speech pattern information, grammar usage, voice identification information, and so forth.

The method can include the CRM device determining whether the centralized database 102 includes an entry for a caller index ID associated with the caller (226). In one embodiment, the CRM device 100 can identify a caller using identifying information in the call metadata for the caller. The CRM device 100 can use the identifying information to query the centralized database 102 to determine whether any of the entries in the centralized database 102 include identifying information that matches the identifying information from the copy of the digital signal.

In another example, the CRM device 100 can identify a caller using a voice fingerprint. Callers and caller agents 104-108 may desire to maintain caller privacy for the caller and not provide private information to the centralized database 102. In one example, the CRM device 100 can identify a customer without the private information using voice fingerprint identification (ID). A human voice is unique and can be voice printed. The voice fingerprint can be used to find new correlations between previously isolated call metadata, individual personality and behavior data, and transaction data. The centralized database can receive, from a call center 108, an anonymized recording of a caller communication for a caller. The CRM device 100 can access the centralized database 102 and analyze the caller communication to identify the caller using a voice fingerprint. For example, the CRM device 100 can generate a voice fingerprint for the caller using the call metadata and to query the centralized database 102 to determine whether any of the entries in the centralized database 102 include a voice fingerprint that matches the voice fingerprint from the copy of the digital signal.

When the centralized database 102 does not include the entry, the method can include the CRM device 214 generating a caller index ID and a caller profile for the caller (228). The CRM device 214 can associate the caller index ID with the caller profile. When the centralized database 102 does not include the entry, the method can also include adding the call metadata to the caller profile and store the caller profile in the centralized database 102 (230). When the centralized database 102 includes one or more entries for the caller index ID, the method can include the CRM device 214 adding the call metadata to the caller profile associated with the caller index ID (232). For example, the CRM device 214 can add the call metadata to the caller profile by identifying a caller index ID in the centralized database 102 that is associated with the caller. The call data is not intended to be limited to being received from a single electronic device. For example, the CRM device 214 can receive a first digital signal from a first electronic device and process the signal according to steps 224-236. In this example, the CRM device 214 can receive a second digital signal from a second electronic device and also process the second signal according to steps 224-236.

In one example, errors, omissions, and deliberate misinformation can prevent the CRM device 100 from accurately detecting such matches, limiting the CRM device 100 to accurately identifying a caller. Additionally, the call agents 104 108 may each maintain private databases that may contain unique information for a caller, as each call center and/or company doing business with the same caller may have their own contact records for the caller. The CRM device 100 can aggregate caller information at the centralized database 102. As call metadata for different calls and for different callers may be aggregated at the centralized database 102, the caller communications may be anonymized and associated with caller index IDs. The aggregated calls can enable the CRM device 100 to have an increased accuracy level in caller profiling.

In one embodiment, the CRM device 100 can identify a same customer from calls placed by the customer to different call agents 104-108. For example, a person in Texas can make a first call to a first company 106 that provides services in a first industry. In this example, a recording of the call can be stored in the centralized database 102 and the CRM device 100 can generate a voice fingerprint for the call and build a caller profile for the person. At a later date and time, the same person can make a second call a second company 106 that provides services in a second industry. The CRM device 100 can analyze the second call to determine that the caller is the same person based on the voice fingerprint. In this example, the CRM device 100 can send a caller profile to an electronic device used by a CSR of the second company 106. In this example, even though the CSR at the second company 106 had not previously interacted with the person, the CRM device 100 can identify the person using their voice fingerprint and send the caller profile to the CSR of the second company 106. An advantage of the CRM device 100 providing the previous caller profile information to the CSR of the second company can be to provide the CSR with a caller profile for the CSR to use to adjust their interactions with the caller during the call.

As discussed in greater detail in the proceeding paragraphs, the CRM device 100 can identify a same customer from calls placed by the customer to different call agents 104-108 using voice fingerprints. For example, a voice fingerprint can be used as a key by the CRM device 100 to identify a caller profile for a customer who may have interacted with multiple call agents 104-108. An advantage of using the voice fingerprints as the key can be to void misidentifications or errors caused by mistakes or deviations in contact data of a customer. For example, a caller may interact with a first CSR of a first company and a second CSR of a second company. In this example, the caller's name may be John Smith and a first CSR may spell the name Jon Smith and a second CSR may spell the name John Smit. By using the voice fingerprint of the caller as the key, a caller profile can be identified for John Smith even when the first CSR and the second CSR may both have made mistakes in the customer's identifying information.

In one example, when the CRM device 100 compares the received identifying information to the stored identifying information, the CRM device can determine when there may be errors in the identifying information from the call metadata and/or the identifying information stored in the centralized database 102. For example, the identifying information from the call metadata or the centralized database 102 can include a misspelled name or other incorrect information. In this example, when the CRM device 100 compares the identifying information from the call metadata to the identifying information in the centralized database 102, the CRM device 100 can determine that at least a portion of the identifying information from the call metadata that does not match the identifying information in the database.

In one embodiment, the CRM device 100 can correct mismatching identifying information. For example, to correct the erroneous information, the CRM device 100 can weigh the identifying information in the centralized database 102 and the identifying information in the call metadata. In one example, the more recent identifying information from the call metadata can be weighted more heavily than the identifying information in the centralized database 102. In another example, when there the identifying information in the centralized database 102 is aggregated from multiple calls, the CRM device 100 can weigh the identifying information in the centralized database 102 more heavily than the identifying information in the call metadata. The CRM device 100 can select the identifying information that is weighted more heavily and change the mismatching identifying information using the more heavily weighted information.

In another example, the CRM device 100 can communicate a notification to a CSR indicating that the received identifying information may be incorrect and request that the CSR verify the identifying information. In another example, the CRM device 100 can send a recommendation for correcting the identifying information to the electronic device 212. For example, a credit card bureau may incorrectly associate a transaction with a customer. In this example, the CRM device 100 can determine that the voice fingerprint for the customer with the credit report may not match a voice fingerprint for the customer who performed the transaction. The CRM device 100 can communicate to the credit card bureau the error and the credit card bureau can correct the mistake.

In one embodiment, when the CRM device 100 can contact a device associated with a customer to request authorization to correct the error can identify a potential error. In another embodiment, the CRM device 100 can contact a device associated with a customer to request corrected identifying information. For example, the CRM device 100 can send an automated text to a smartphone of a customer or send an email to an email address of a customer requesting corrected identifying information. When the CRM device 100 received the corrected information, the CRM device 100 can update the identifying information in the centralized database 102 accordingly.

The method can include determining the CRM device 214 determining whether the centralized database 102 includes a threshold amount of call metadata for the caller profile (234). The threshold amount of call metadata to determine whether the centralized database 102 includes a threshold amount of call metadata for the caller profile can be determined using a learning algorithm. In one embodiment, the CRM device 214 can initially assign a first weight to the voice fingerprints and a second weight to identifying information. In one example, the identifying information can initially be weighted more heavily than the voice fingerprints. In this example, threshold amount of call metadata can be a predefined amount of identifying information. For example, the centralized database 102 can store information from the call metadata in different data fields and when a defined number of fields (such as 80 percent) contain identifying information, the threshold amount of call metadata is met the CRM device 214 can switch from a training mode to an active mode. The learning algorithm can also evaluate different data in the call metadata and score the different data in the call based on the data's reliability or predictive nature. In one example, the learning algorithm can determine the reliability or predictive nature by analyzing past call metadata to determine what data of the call metadata is used to determine a caller profile (as discussed in greater detail in the proceeding paragraphs) and can reassign weights for the data with a higher level of reliability or predictive nature. For example, the learning algorithm can determine that the voice fingerprint and speech pattern data of a caller has a higher reliability or predictive nature than the identifying information and can adjust a weighting of the information to be greater for the voice fingerprint and speech pattern data.

For example, when the database does not include an entry for the caller index ID, the CRM device 214 can be in a training mode for the caller. The training mode is a mode where the caller profile is not active because there is insufficient call metadata for the CRM device 214 to generate a caller profile for the caller. In one example, when the CRM device 214 is in the training mode, the CRM device 214 may not send a caller profile to a device to display to a CSR. In another example, when the CRM device 214 is in the training mode, the CRM device 214 may send a caller profile to a device to display to a CSR but may flag the caller profile as an initial caller profile that may or may not be accurate.

When in training mode, the CRM device 214 can iteratively add call metadata to the caller profile of the caller each time the CRM device 214 receives a copy of a call for the caller. The CRM device can continue to run in training mode until the centralized database 102 includes the threshold amount of call metadata for the caller profile. When the centralized database 102 includes the threshold amount of call metadata for the caller profile, the CRM device 214 can switch from the training mode to an active mode (236). In one example, when the CRM device 214 is in active mode, a threshold accuracy or quality level of the call metadata may be required for the CRM device to update the caller profile.

FIG. 2B illustrates the centralized database 102 with different access layers 240-250 according to one embodiment. Some numbers in FIG. 2B are similar to some numbers in FIGS. 1 and 2A as noted by similar reference numbers unless expressly described otherwise. The centralized database 102 can store data including: call metadata for multiple callers, caller profiles for multiple callers, identifying information for multiple callers, company information, call center information, and so forth. Different portions of the data or different types of data can have different authorization levels. For example, different users may have varying authorization level clearances to access the different portions of the data or the different data types.

The different users can include: an individual, a company, a government entity, a system administrator, and so forth. In one example, the information included in the caller profiles may be anonymized, where the information included in the caller profiles do not include any sensitive data associated with callers, such as caller phone numbers, social security numbers, addresses, credit card information, and so forth. Where the information included in the caller profiles is anonymized, the information included in the caller profiles may be designated as having a universal access authorization level 242. The universal access authorization level 242 can enable all users to access the information included in the caller profiles.

In another example, the identifying information may be designated as having a limited access authorization level 244. The identifying information can be information received from an input device coupled to the electronic device 212. In one example, the input device can be a voice recognition device that can convert voice data from a call into text information. In another example, the input device can be a graphical user interface (GUI), a touch screen, a keyboard, or a mouse that a CSR uses to input information from a caller during or after a call. The limited access authorization level 244 can enable designated or predefined companies to access the identifying information.

In one embodiment, the centralized database 102 can store identifying information for caller. To maintain anonymity of the caller, the centralized databased 102 can provide a third party (such as a CSR of a call center 108) with a caller profile associated with the caller while preventing the third party from accessing identifying information associated with the caller. For example, a company may receive a call from a customer regarding a sales inquiry. The company may desire to receive a caller profile for the customer to understand a baseline personality for the customer.

The CRM device 100 can determine an identity of the customer using a voice fingerprint and/or identifying information from a call with the customer. In one example, the CRM device 100 can analyze call metadata for a call to determine a first voice fingerprint for a caller of the call. The CRM device 100 can query voice fingerprints stored in the centralized database 102 to find a second voice fingerprint that matches the first voice fingerprint. The second voice fingerprint can be associated with a caller index ID and a caller profile of a caller. When a match is identified, the CRM device 100 can retrieve the caller profile for the caller and send the caller profile to the electronic device 212.

In another example, the CRM device 100 can analyze call metadata for a call to determine identifying information for a caller of the call. The CRM device 100 can query identifying information stored in the centralized database 102 to find identifying information in the centralized database 102 that matches the identifying information from the call metadata. The identifying information in the centralized database 102 can be associated with a caller index ID and a caller profile of a caller. When a match is identified, the CRM device 100 can retrieve the caller profile for the caller and send the caller profile to the electronic device 212. In another example, the CRM device 100 can match both the voice fingerprint and identifying information from the call metadata with a voice fingerprint and identifying information in the centralized database 102 to identify a caller profile. In the preceding examples, the CRM device can utilized the voice fingerprint and/or identifying information stored in the centralized database 102 to identify the caller profile while avoiding revealing, to the third party, the voice fingerprints and/or identifying information stored in the database. An advantage of providing the third party the caller profile while concealing or withholding the stored voice fingerprint and/or identifying information to the third party can be to enable the third party to determine a baseline personality for a customer while avoiding revealing sensitive information to the third party.

In another example, the call center information may be designated as having a restricted access authorization level 246. The restricted access authorization level 246 can enable a government entity access to the identifying information. For example, the government entity can be a police investigator or lawyer with a search warrant, an agent of the federal bureau of investigation (FBI), an agent of the homeland security office, and so forth. In another example, there can be different restricted access authorization levels for the centralized database 102. For example, the centralized database 102 can include a first restricted access authorization level 246 accessible by any law enforcement officer and a second restricted access authorization level 248 that is only accessible to a law enforcement officer with a warrant. The other information, such as algorithms used to determine a caller profile, can be designated as having a classified access authorization level 250, where only a system administrator can access the classified access authorization level 250.

Figure 3:
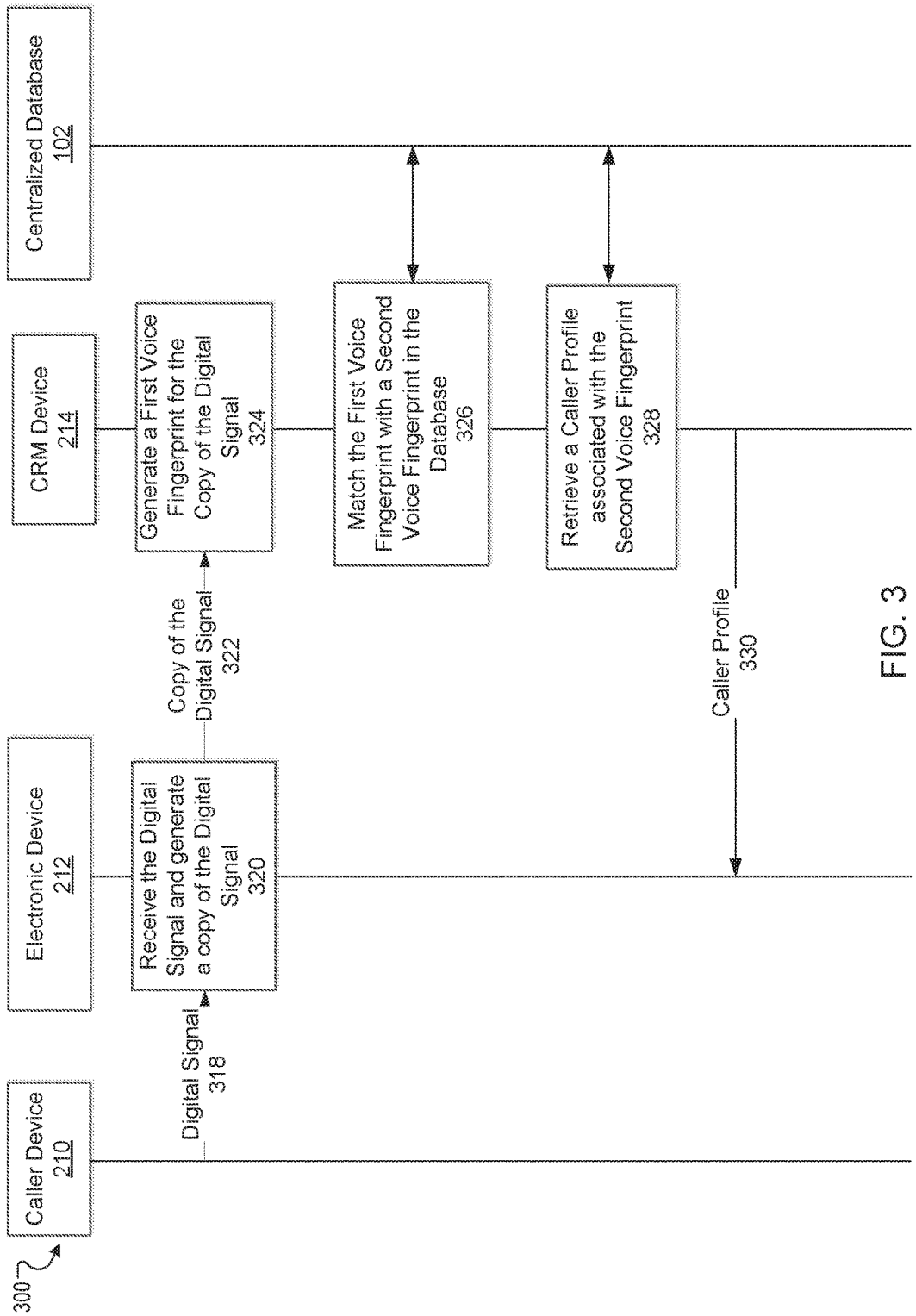
FIG. 3 illustrates a diagram of a method for identifying a caller profile for a caller using a voice fingerprint according to one embodiment.

FIG. 3 illustrates a diagram of a method 300 for identifying a caller profile for a caller using a voice fingerprint according to one embodiment. The method 300 may at least partially be performed by processing logic that includes hardware (e.g., circuitry, dedicated logic, programmable logic, microcode, etc.), software (e.g., instructions executed by a processing device), firmware or a combination thereof. The method 300 may be performed by all or part of the CRM device 100 of FIG. 1. For example, the method 300 may be performed by all or part of the processor 110 (FIG. 1) or the communication device 112 (FIG. 1). Some numbers in FIG. 3 are similar to some numbers in FIGS. 1, 2A, and 2B as noted by similar reference numbers unless expressly described otherwise.

Referring to FIG. 3, the method 300 begins with the caller device 210 placing a call to an electronic device 212 (318). The method can include the electronic device 212 receiving the digital signal representative of the call from the caller device and generating a copy of the digital signal (320). The method can include the electronic device 212 sending the copy of the digital signal to the CRM device 214 (322). The method can include the CRM device 214 generating a first voice fingerprint for the copy of the digital signal (324). In one embodiment, the CRM device 214 can generate the first voice fingerprint by determining different speech elements of a call. The speech elements can include: a dialect of the caller, a sound of the caller's voice, a speech pattern of the caller, a rhythm of individual's voice, a pitch of the caller's voice, a speed of the caller's speech, spectral magnitudes of the caller's voice, a frequency of the caller's voice, and so forth. In one example, the CRM device 214 can determine one or more of the speech elements for the copy of the digital signal and compare the speech elements with speech elements of voice fingerprints in the centralized database 102. In one embodiment, the CRM device 214 can employ a multifactor analysis using multiple speech elements in matching voice fingerprints. In one example, the CRM device 214 can match words uniquely used by the user (such as slang, words not commonly used by the general public, and mispronounced words) or a dialect of the user with speech elements unrelated to the content of the digital signal, such as a pitch of the caller's voice, a speed of the caller's speech, spectral magnitudes of the caller's voice, or a frequency of the caller's voice.

The method can include matching the first voice fingerprint with a second voice fingerprint in the centralized database 102 (326). The method can include retrieving a caller profile associated with the second voice fingerprint (328). The method can include sending the caller profile to the electronic device 212 (330).

Figure 4:
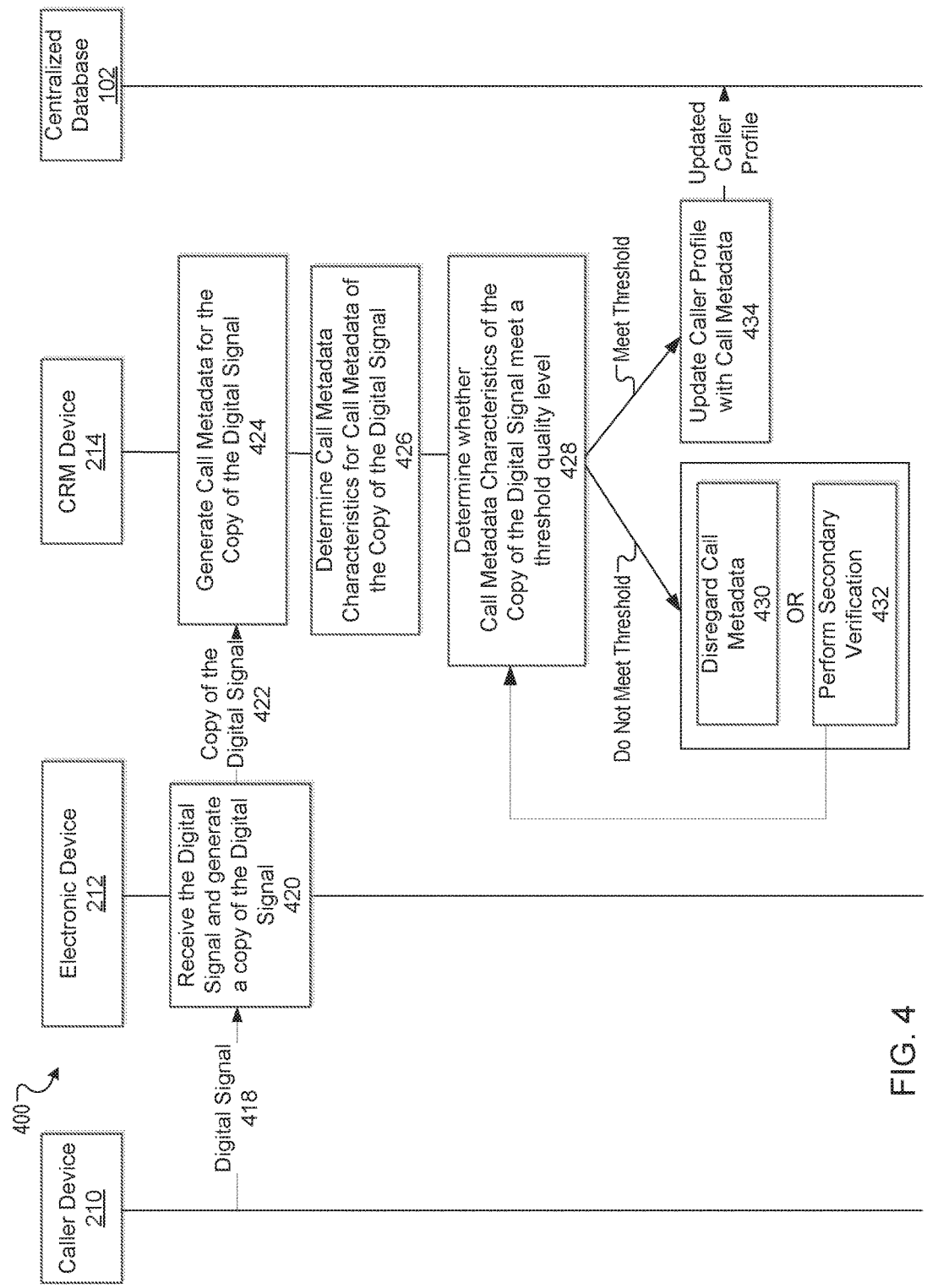
FIG. 4 illustrates a diagram of a method for determining a quality level of a call according to one embodiment.

FIG. 4 illustrates a diagram of a method 400 for determining a quality level of a call according to one embodiment. The method 400 may at least partially be performed by processing logic that includes hardware (e.g., circuitry, dedicated logic, programmable logic, microcode, etc.), software (e.g., instructions executed by a processing device), firmware or a combination thereof. The method 400 may be performed by all or part of the CRM device 100 of FIG. 1. For example, the method 400 may be performed by all or part of the processor 110 (FIG. 1) or the communication device 112 (FIG. 1). Some numbers in FIG. 4 are similar to some numbers in FIGS. 1, 2A, and 2B as noted by similar reference numbers unless expressly described otherwise.

Referring to FIG. 4, the method 400 begins with the caller device 210 placing a call to an electronic device 212 (418). The method can include the electronic device 212 receiving a digital signal representative of the call from the caller device 210 and generating a copy of the digital signal (420). The method can include the electronic device 212 sending the copy of the digital signal to the CRM device 214 (422). The method can include the CRM device 214 generating call metadata for the copy of the digital signal (424). The method can include the CRM device 214 determining call metadata characteristics for call metadata of the copy of the digital signal (426). The method can include the CRM device 214 determining whether call metadata characteristics of the copy of the digital signal meet a threshold quality level (428).

When the CRM device 100 analyzes a call metadata, the CRM device 100 can determine a voice fingerprint for a caller with a threshold quality level of identification accuracy based on call metadata characteristics. The call metadata characteristics can include: an audio quality level of the call, a volume level of the call, a length of the call, and so forth. In one example, the threshold quality level can be 15 decibels for the volume level and 30 second for the length of the call. In one example, when the call metadata characteristics of the copy of the digital signal may be below the threshold quality level, the CRM device 100 may determine that several voice fingerprints that are stored in the centralized database 102 may match voice fingerprint for the current digital signal.

In one embodiment, when the call metadata characteristics do not meet the threshold quality level, the CRM device can disregard the call metadata of the copy of the digital signal (430). In another embodiment, when the call metadata characteristics do not meet the threshold quality level, the CRM device 214 can perform a secondary verification of the call metadata (432).

In one embodiment, when the identification accuracy is below the threshold level, the CRM device 100 can use identifying information associated with the voice fingerprint to increase the ID accuracy level. The identifying information can include a name of the caller, an age of the caller, a gender of the caller, a location of the caller, a nationality of the caller, and so forth. In one example, the CRM device 100 and/or the centralized database 102 can receive the identifying information via an input device. For example, as a CSR is on a call with a customer, the CSR can ask customer profile questions and input the answers into the CRM device 100 and/or the centralized database 102 via an input device, such as a graphical user interface (GUI), a mouse, a keyboard, a touch-screen interface, and so forth.

In another embodiment, the secondary verification can include the CRM device 214 flagging the call metadata to be analyzed by a reviewer, such as a user or system administrator. In another example, the secondary verification can include the CRM device 214 filtering the copy of the digital signal for noise or distortion and then determining whether the call metadata characteristics of the filtered copy of the digital signal meet the threshold quality level.

When the call metadata characteristics of the copy of the digital signal meet the threshold quality level, the CRM device 214 can update a caller profile of a caller with the call metadata (434). For example, the CRM device 214 updating the caller profile in the centralized database 102 by adding the call metadata to the caller profile in the centralized database 102.

In another embodiment, the CRM device 100 can weigh the voice fingerprint and the identifying information based on the call criteria. For example, when the digital signal quality exceeds a threshold quality level (e.g., good digital signal quality) the CRM device 100 can weight the voice fingerprint more heavily than the identifying information. In another example, when the digital signal quality decreases below a threshold quality level (e.g., bad digital signal quality) the CRM device 100 can weight the voice fingerprint less heavily than the identifying information. In another example, when the digital signal quality decreases below the threshold quality level, the CRM device 100 can tag the call metadata as needing further analysis. In one embodiment, when the call metadata may be tagged as needing further analysis, the CRM device 100 can receive user input to clarify the call metadata. For example, a CSR that may be a party on the call can score a caller in real time or manually input identifying information. In another embodiment, when the call metadata is tagged as needing further analysis, the CRM device 100 can designate the tagged call metadata for human review and an individual can review the tagged call metadata. When the human reviews the tagged call metadata, an input device (such as a graphical user interface) can receive review or caller profile information from the user and update a caller profile accordingly.

Figure 5:
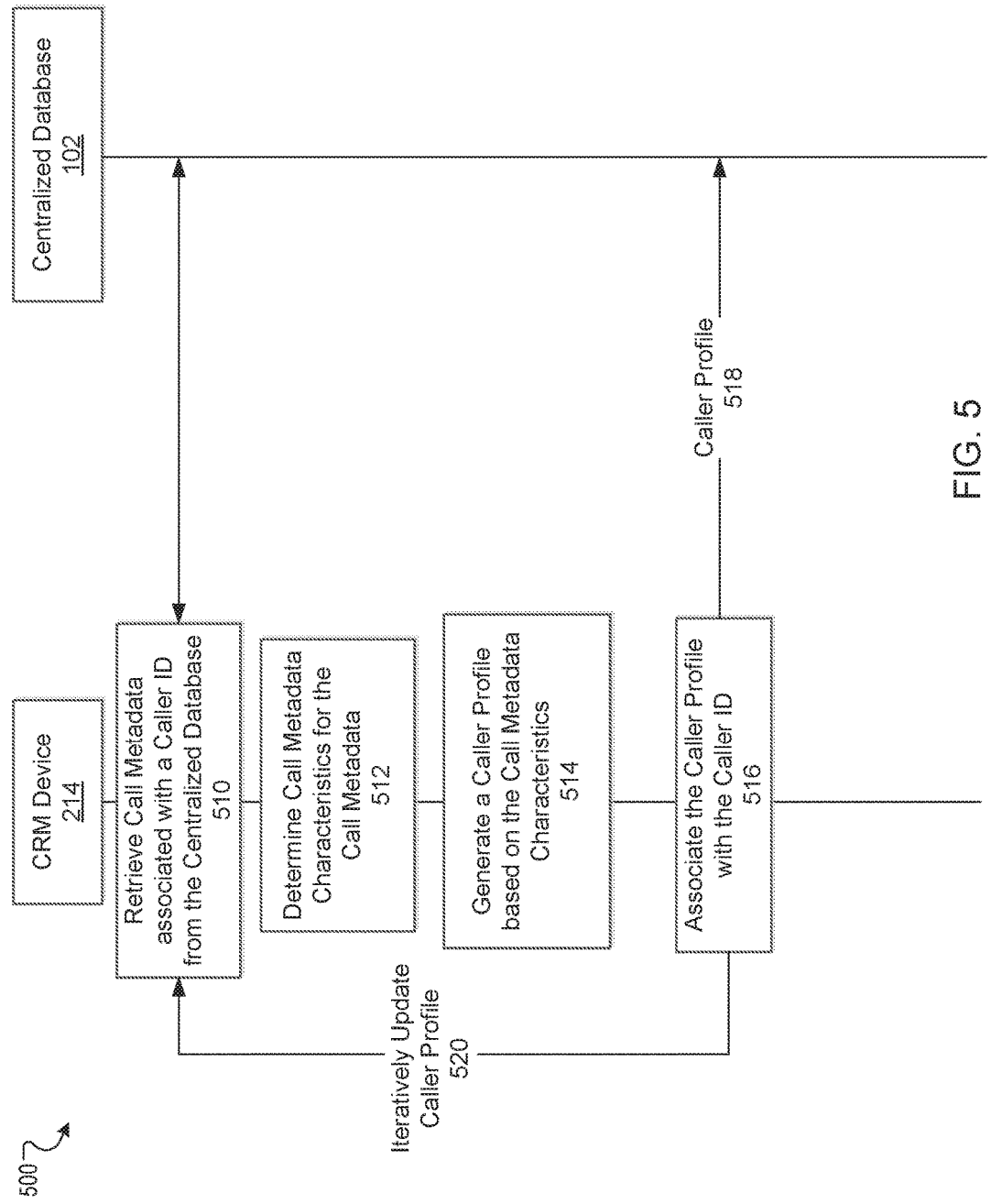
FIG. 5 illustrates a diagram of a method for determining a caller profile of a caller according to one embodiment.

FIG. 5 illustrates a diagram of a method 500 for determining a caller profile of a caller according to one embodiment. The method 500 may at least partially be performed by processing logic that includes hardware (e.g., circuitry, dedicated logic, programmable logic, microcode, etc.), software (e.g., instructions executed by a processing device), firmware or a combination thereof. The method 500 may be performed by all or part of the CRM device 100 of FIG. 1. For example, the method 500 may be performed by all or part of the processor 110 (FIG. 1) or the communication device 112 (FIG. 1). Some numbers in FIG. 5 are similar to some numbers in FIGS. 1, 2A, and 2B as noted by similar reference numbers unless expressly described otherwise.

Referring to FIG. 5, the method 500 begins with the CRM device 214 retrieving call metadata associated with a caller index ID from the centralized database 102 (510). The method can include the CRM device 214 determining call metadata characteristics for the call metadata (512). The method can include the CRM device 214 generating a caller profile based on the call metadata characteristics (514). To determine the caller profile, the CRM device 214 can evaluate the call metadata using a psychological behavioral model. Psychological behavioral models can be used to evaluate and understand how and/or why a person interacts with another person. For example, a Process Communication Model® ("PCM") assumes that people fit into one of six basic personality types: a reactor, a workaholic, a persister, a dreamer, a rebel, or a promoter. Individuals with the different six personality types may learn differently, be motivated differently, communicate differently, and/or have different sequences of negative behaviors when they may be in distress. Individuals with the different PCM personality types may respond differently to positive or negative communications, such as communications with different tones and/or messages. Understanding of a caller's profile (such as their behavior or personality type) can provide guidance to a CSR regarding is an appropriate responsive tone or message to use when engaging the caller.

In another example, the CRM device 100 can access and analyze call metadata from a call in real-time (e.g., streaming call metadata as the call is occurring) or in near real-time (e.g., call metadata streamed with a delay). An advantage of analyzing the caller communication in real-time can be that storing the caller communication at the centralized database 102 may be avoided and complete anonymity can be maintained. For example, as the CRM device 100 analyzes the caller communication in real time, the CRM device 100 can determine the caller profile associated with the caller while avoiding storing of sensitive information. In another example, the CRM device 100 and/or the centralized database 102 can buffer the call metadata for a period of time until the CRM device 100 can process the caller data. In this example, when the CRM device 100 has processed the call metadata, the buffered call metadata can be deleted or discarded. In one example, the CRM device 100 may store call metadata in an anonymized or non-anonymized format based on a regulation for an area the caller may be calling from and/or an area a customer may be calling to.

The CRM device 214 can match call metadata characteristics of the call metadata with characteristics associated with a personality type of the psychological behavioral model for a caller profile. For example, the call metadata characteristics and the characteristics associated with the psychological behavioral model can include terminology and vocabulary used in the call metadata, a speed of speech in the call metadata, a range of speech volume of the call metadata, a repetition of words in the call metadata, a voice frequency range in the call metadata, and so forth. The CRM device 214 can determine a number of call metadata characteristics that match the characteristics associated with the psychological behavioral model and select the personality type for the psychological behavioral model with the highest number of matches. In one example, the CRM device 214 can select more than one personality types for the caller profile.

The caller profile can include user information, such as a personality type of the caller, brand preferences, gender information, buying preferences, frequently of keywords used by the caller, and so forth. In one example, the personality types can include: extravert, introvert, mechanical or analytical, nurturing, generous, selfish, and so forth. In one example, a personality type of a caller can be determined based on a length of the call, a tone of voice used during the call, keywords used during the call, a speed of the caller's speech, a frequency of keywords used during the call, and so forth. In another example, the personality type of the caller can be determined by the CRM device 100 receiving caller responses to predetermined or predictive questions or keywords seeded within a conversation. For example, a CSR selling a life insurance plan to a caller may seed within the conversation an aggressive statement such as, "If you don't buy now, the offer is off the table." In this example, the caller may react positively, negatively, or indifferently toward the statement and the CRM device can refine a caller profile in view of the caller's reaction.

In another example, the personality type of the caller can be determined by the CRM device 100 receiving secondary data, such as a time of day, a length of call, a hold time, and many other factors that can be compared to mood and call outcome, across events utilizing voice fingerprint as a link between otherwise isolated pools of data for the same caller's interactions with many companies over time.

The method can include the CRM device 214 associating the caller profile with the caller index ID (516). In one example, the caller profile can be set as a behavior baseline profile for the caller associated with the caller index ID. The method can include the CRM device storing the caller profile with the associated caller index ID in the centralized database 102 (518).

In another example, the CRM device 100 can iteratively update the caller profile as additional calls may be identified and analyzed for the same voice fingerprint (520). As a number of calls may be analyzed for the same voice fingerprint, an accuracy of the caller profile, such as the personality type of the caller, can increase. For example, when a first call is received for a caller, a baseline caller profile can be created. The baseline caller profile can have a first threshold accuracy level (e.g., a confidence score). When a second call may be received for the caller, the caller profile can be updated for that caller and an accuracy level for the caller profile can increase to a second threshold accuracy level. In another example, the CRM device 100 can send the accuracy level of the caller profile along with the caller profile to a CSR. In another example, the CRM device 100 associate the accuracy level of the caller profile with the caller profile and store it in the centralized database 102.

Figure 6:
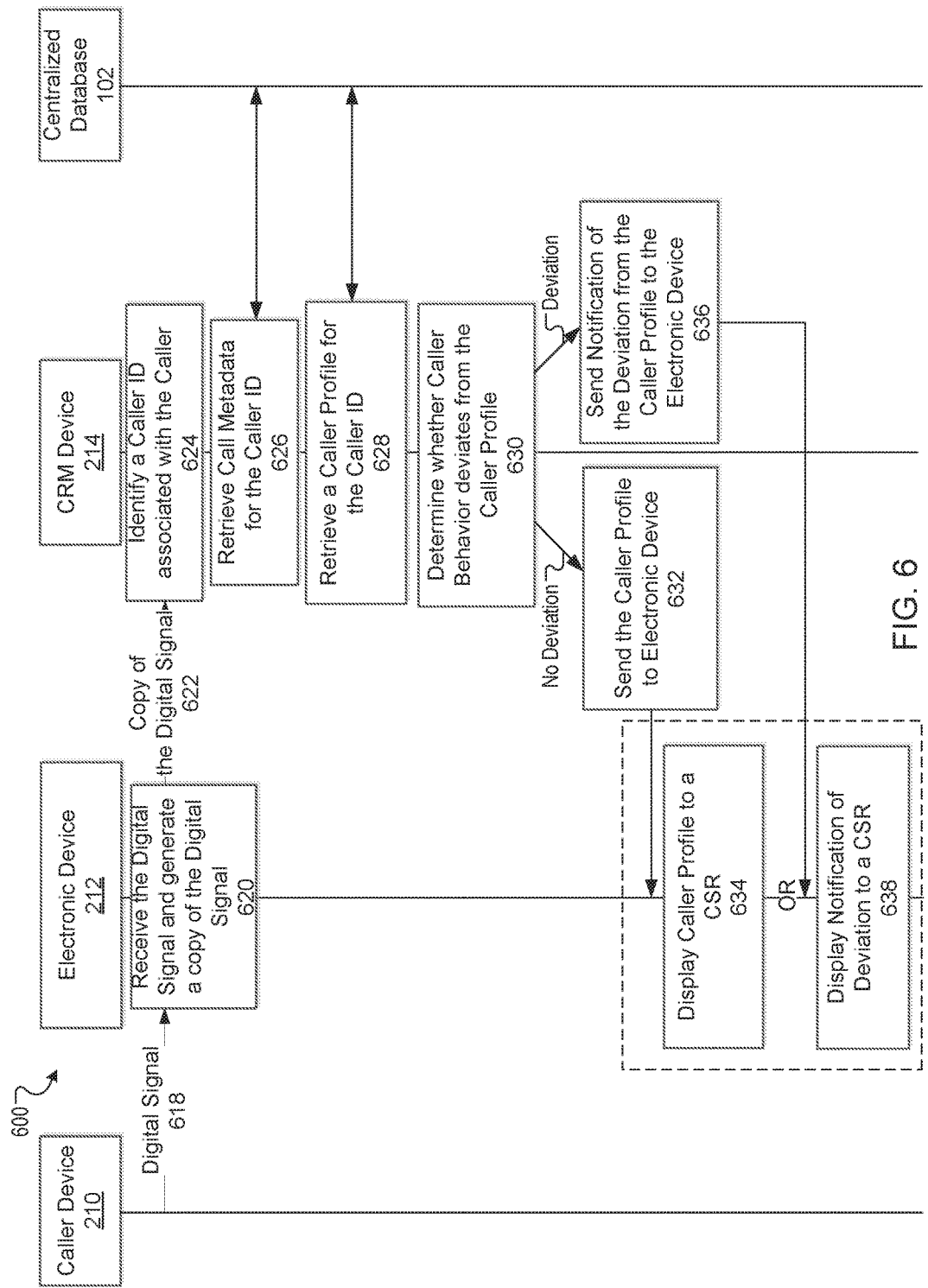
FIG. 6 illustrates a diagram of a method for determining when a behavior of a caller deviates from a caller profile according to one embodiment.

FIG. 6 illustrates a diagram of a method 600 for determining when a behavior of a caller deviates from a caller profile according to one embodiment. The method 600 may at least partially be performed by processing logic that includes hardware (e.g., circuitry, dedicated logic, programmable logic, microcode, etc.), software (e.g., instructions executed by a processing device), firmware or a combination thereof. The method 600 may be performed by all or part of the CRM device 100 of FIG. 1. For example, the method 600 may be performed by all or part of the processor 110 (FIG. 1) or the communication device 112 (FIG. 1). Some numbers in FIG. 6 are similar to some numbers in FIGS. 1, 2A, and 2B as noted by similar reference numbers unless expressly described otherwise.

Referring to FIG. 6, the method 600 begins with the caller device 210 placing a call to an electronic device 212 (618). The method can include the electronic device 212 receiving a digital signal representative of the call from the caller device 210 and generating a copy of the digital signal (620). The method can include the electronic device 212 sending the copy of the digital signal to the CRM device 214 (622). The method can include the CRM device 214 identifying a caller index ID associated with a caller talking in the copy of the digital signal (624). The method can include the CRM device 214 retrieving call metadata for the caller index ID from the centralized database 102 (626). The method can include the CRM device 214 retrieving a caller profile associated with the caller index ID from the centralized database 102 (628).

The method can include the CRM device 214 determining whether a caller's behavior deviates from the caller profile (630). In one embodiment, the CRM device 214 can determine whether the caller's behavior deviates from the caller profile by matching call metadata characteristics for the copy of the call with the call metadata characteristics of the retrieved caller profile. When a threshold number of call metadata characteristics for the copy of the call matches the call metadata characteristics for the retrieved caller profile, the caller behavior does not deviate from the caller profile. When the threshold number of call metadata characteristics for the copy of the call does not match the call metadata characteristics for the retrieved caller profile, the caller behavior deviates from the caller profile. In another example, the CRM device 214 can detect how a caller feels about a brand of a company and if the caller may now feel more or less positive toward the brand than the caller did in the past. A large volume of calls, linked back to many past reference points, can reveal anonymized information about a performance of an entire brand or advertising campaign. In one example, the CRM device 100 can use multiple caller communications to generate key scoring criteria for call metadata. For example, while the call metadata may include tens or hundreds of different call metadata characteristics, the CRM device 100 may determine that only a portion of the call metadata characteristics vary from caller to caller. In this example, the CRM device 100 may only use the call metadata characteristics that vary from caller to caller when determining a caller profile or a deviation of the caller from the caller profile.

When the caller behavior does not deviate from the caller profile, the method can include sending the caller profile to the electronic device 212 (632). The method can include the electronic device 212 displaying the caller profile to a CSR via a display device (634). When the caller behavior deviates from the caller profile, the method can include the CRM device 214 sending, to the electronic device 212, a notification of the deviate from the caller profile (636). The method can include the electronic device 212 displaying the notification to the CSR via the display device (638). In one embodiment, the CRM device 214 can determine a new caller profile for the caller behavior according to the method 500. The CRM device 214 can send the new caller profile to the electronic device 212 to display to the CSR via the display device.

In one example, the CSR or a company may benefit from taking advantage of deviations between a caller's current behavior and a past behavior of the caller. In another example, the CSR or a company may benefit from being warned about deviations between a caller's current behavior and a past behavior of the caller. For example, a caller may typically have a subdued personality where the caller speaks in a quite or timid voice and is not very excitable. The CRM device 214 can display to the CSR via the display device of the electronic device 212 a baseline for the caller. The CSR can adjust their interactions with the customer for that baseline or for a deviation from the baseline. For example, when the CRM device 214 indicates to the CSR that a caller normally has a subdued personality and during a current interaction with the caller the caller may be vocal and agitated, the CSR can adjust their interaction with the caller to calm the caller down. In another example, when the baseline for the caller may be a vocal and agitated personality, when the caller calls in and may be vocal and agitated, the CSR can interact with the customer normally without special care to calm the customer down.

Figure 7:
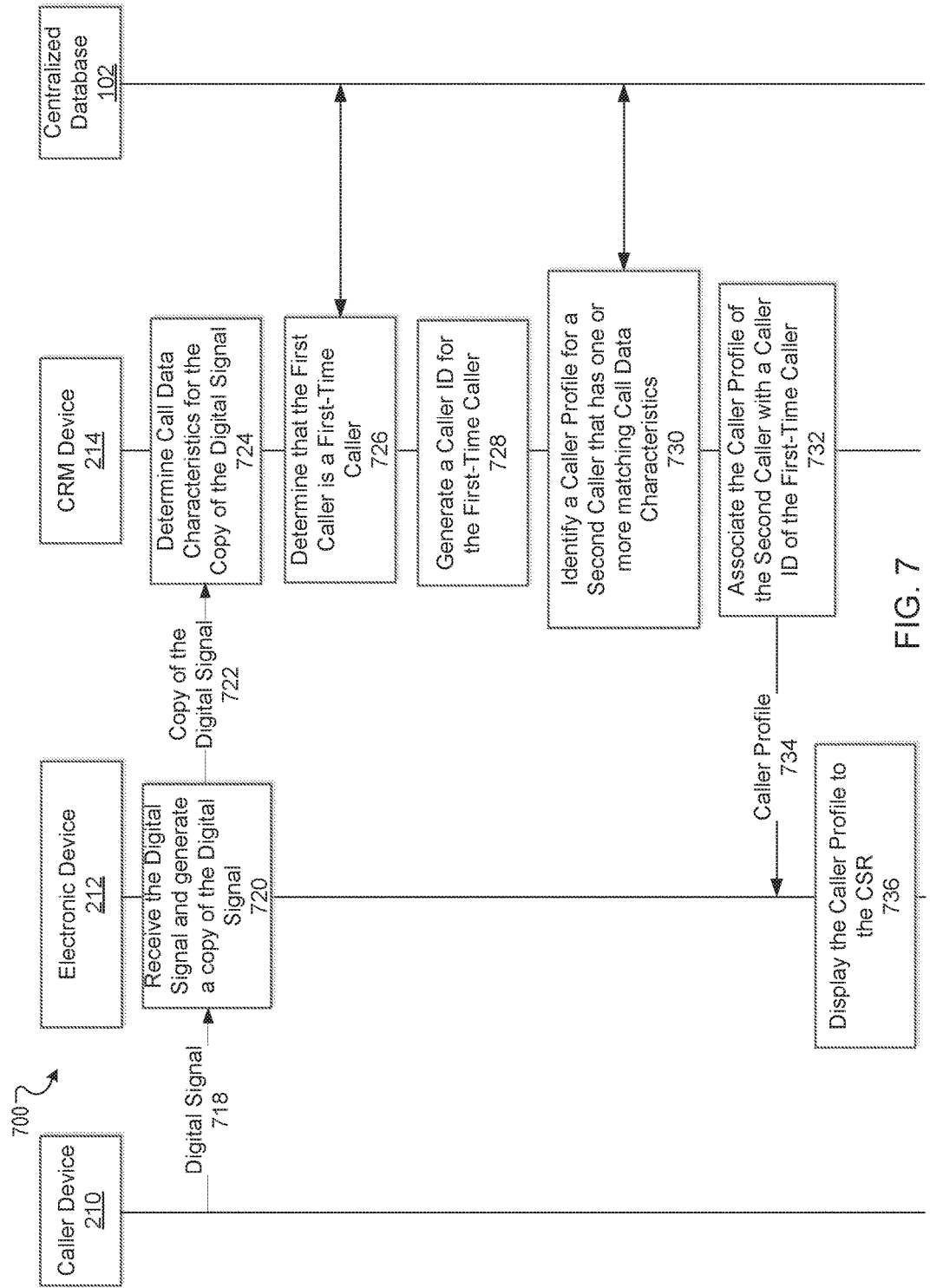
FIG. 7 illustrates a diagram of a method for determining when a behavior of a caller deviates from a caller profile according to one embodiment.

FIG. 7 illustrates a diagram of a method 700 for determining when a behavior of a caller deviates from a caller profile according to one embodiment. The method 700 may at least partially be performed by processing logic that includes hardware (e.g., circuitry, dedicated logic, programmable logic, microcode, etc.), software (e.g., instructions executed by a processing device), firmware or a combination thereof. The method 700 may be performed by all or part of the CRM device 100 of FIG. 1. For example, the method 700 may be performed by all or part of the processor 110 (FIG. 1) or the communication device 112 (FIG. 1). Some numbers in FIG. 7 are similar to some numbers in FIGS. 1, 2A, and 2B as noted by similar reference numbers unless expressly described otherwise.

Referring to FIG. 7, the method 700 begins with the caller device 210 placing a call to an electronic device 212 (718). The method can include the electronic device 212 receiving a digital signal representative of the call from the caller device 210 and generating a copy of the digital signal (720). The method can include the electronic device 212 sending the copy of the digital signal to the CRM device 214 (722). The method can include the CRM device 214 determining call metadata characteristics for the copy of the digital signal (724). The method can include the CRM device 214 determining that the caller is a first-time caller (726). In one example, the CRM device 214 can determine that the caller is a first time caller by determining that the centralized database 102 does not include an entry that includes a voice fingerprint that matches a voice fingerprint of the copy of the call. In another example, the CRM device 214 can determine that the caller is a first time caller by determining that the centralized database 102 does not include an entry that includes identifying information that matches identifying information of the call metadata. The method can include generating a caller index ID for the first-time caller (728). The method can include the CRM device 214 identifying a caller profile for a second caller that has one or more call metadata characteristics that match the call metadata characteristics for the copy of the call (730). The method can include the CRM device 214 associating the caller profile of the second caller with the caller index ID for the first-time caller (732). The method can include the CRM device 214 sending the caller profile to the electronic device 212 (734). The method can include the electronic device 212 displaying the caller profile to a CSR via a display device (736).

Figure 8:
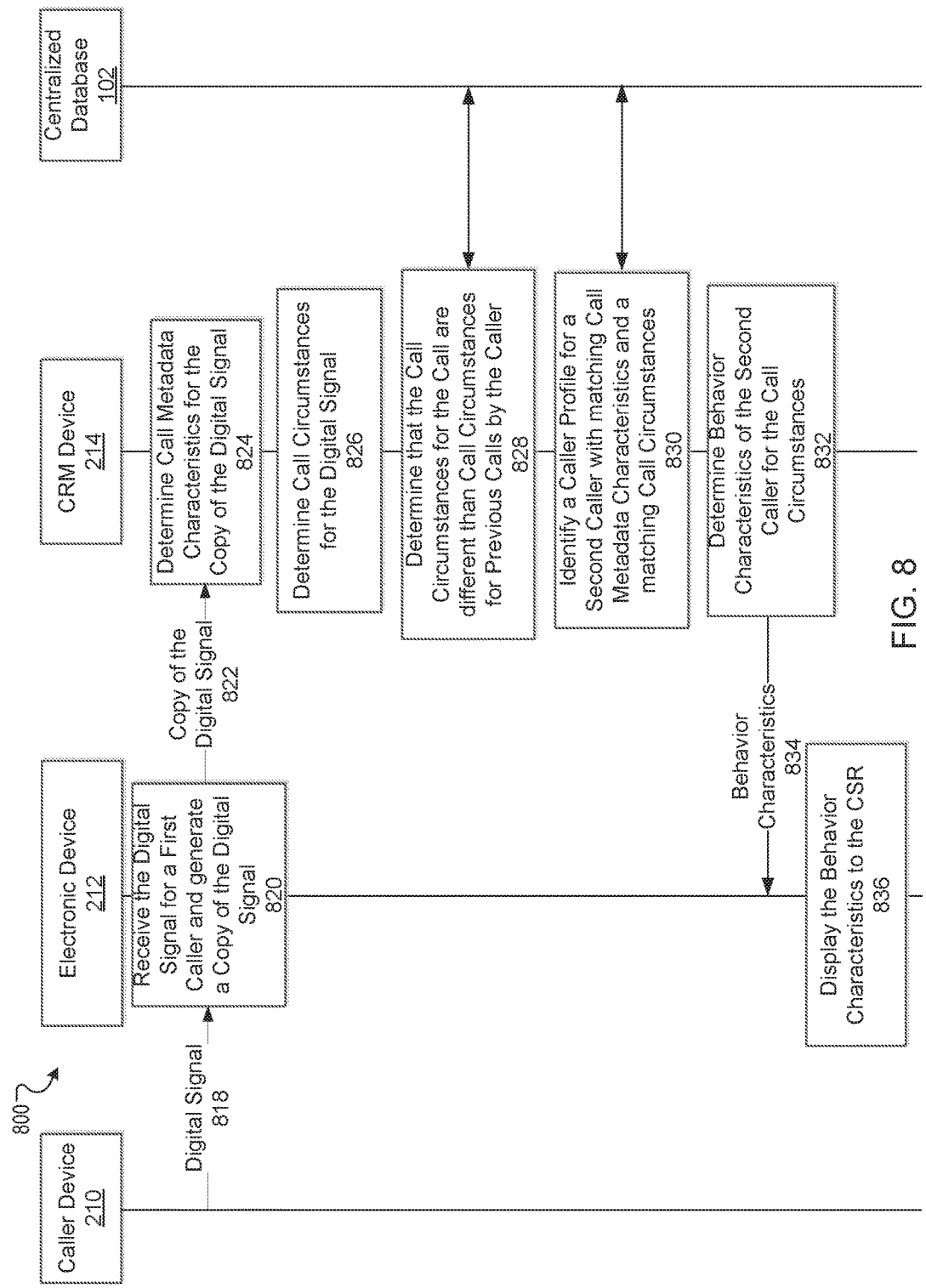
FIG. 8 illustrates a diagram of a method for determining behavior of a caller for different circumstances according to one embodiment.

FIG. 8 illustrates a diagram of a method 800 for determining behavior of a caller for different circumstances according to one embodiment. The method 800 may at least partially be performed by processing logic that includes hardware (e.g., circuitry, dedicated logic, programmable logic, microcode, etc.), software (e.g., instructions executed by a processing device), firmware or a combination thereof. The method 800 may be performed by all or part of the CRM device 100 of FIG. 1. For example, the method 800 may be performed by all or part of the processor 110 (FIG. 1) or the communication device 112 (FIG. 1). Some numbers in FIG. 8 are similar to some numbers in FIGS. 1, 2A, and 2B as noted by similar reference numbers unless expressly described otherwise.

Referring to FIG. 8, the method 800 begins with the caller device 210 placing a call to an electronic device 212 (818). The method can include the electronic device 212 receiving a digital signal representative of the call from the caller device 210 and generating a copy of the digital signal (820). The method can include the electronic device 212 sending the copy of the digital signal to the CRM device 214 (822). The method can include the CRM device 214 determining call metadata characteristics for the copy of the call (824). The method can include the CRM device 214 determining call circumstances for the copy of the call (826).

To determine the call circumstances, the CRM device 100 can categorize or tag information in the caller profile with event information. For example, when a customer calls regarding buying a product, the CRM device 100 can tag behavioral information for the call with a sales event. In one embodiment, when a customer calls regarding a product complaint, the CRM device 100 can tag behavioral information for the call with a customer service event. The CRM device 100 can use the categories or tag to correlate different behavioral baselines for a customer with the different events. In one embodiment, the call metadata can include the event information, such as when an input device coupled to the electronic device receives event information from a CSR.

In another embodiment, the CRM device 214 can analyze the call metadata for keywords or other information to determine the event information. For example, the CRM device 100 can identify keywords during a conversation between a caller and a CSR to identify the situation or event. In another embodiment, the CRM device 100 can identify a situation or event by identifying the number the caller is dialing to, such as a customer service number, a sales number, a product repair number, and so forth. An advantage of categorizing or tagging behavioral information of the caller profile for different events can be to refine the caller profile for different events to more accurately ascertain a baseline for the caller under different situations. Another advantage of categorizing or tagging behavioral information of the caller profile for different events can be to provide a CSR with real-time behavioral baseline information for varying situations and events. For example, a caller can have an aggressive nature when haggling for a price of a product and a calm nature when calling a bank for financial information. The CRM device 100 can analyze the call to identify the situation or events surrounding the call and provided a refined or adjusted caller profile for the caller.

The method can include the CRM device 214 determining that the call circumstances for the copy of the call are different than call circumstances for previous calls by the caller (828). The method can include the CRM device 214 can identifying a caller profile for a second caller with call metadata characteristics that matches call metadata characteristics and call circumstances of the copy of the call (830). The method can include determining behavior characteristics of the second caller for the call circumstances (832).

In one example, the CRM device 100 can compare caller profiles for different callers to predict a behavior for a given caller. For example, a first caller may not have previously called a company regarding an inquiry for legal services. However, a second caller with a similar caller profile to the first customer may have previously called the company regarding an inquiry for legal services. In this example, the CRM device 100 can predict the first caller's behavior when discussing the legal services based on the second caller's previous behavior.

The method can include the CRM device 214 sending the behavior characteristics to the electronic device 212 (834). The method can include the electronic device 212 displaying the behavior characteristics to a CSR via a display device of the electronic device 212 (836).

Figure 9:
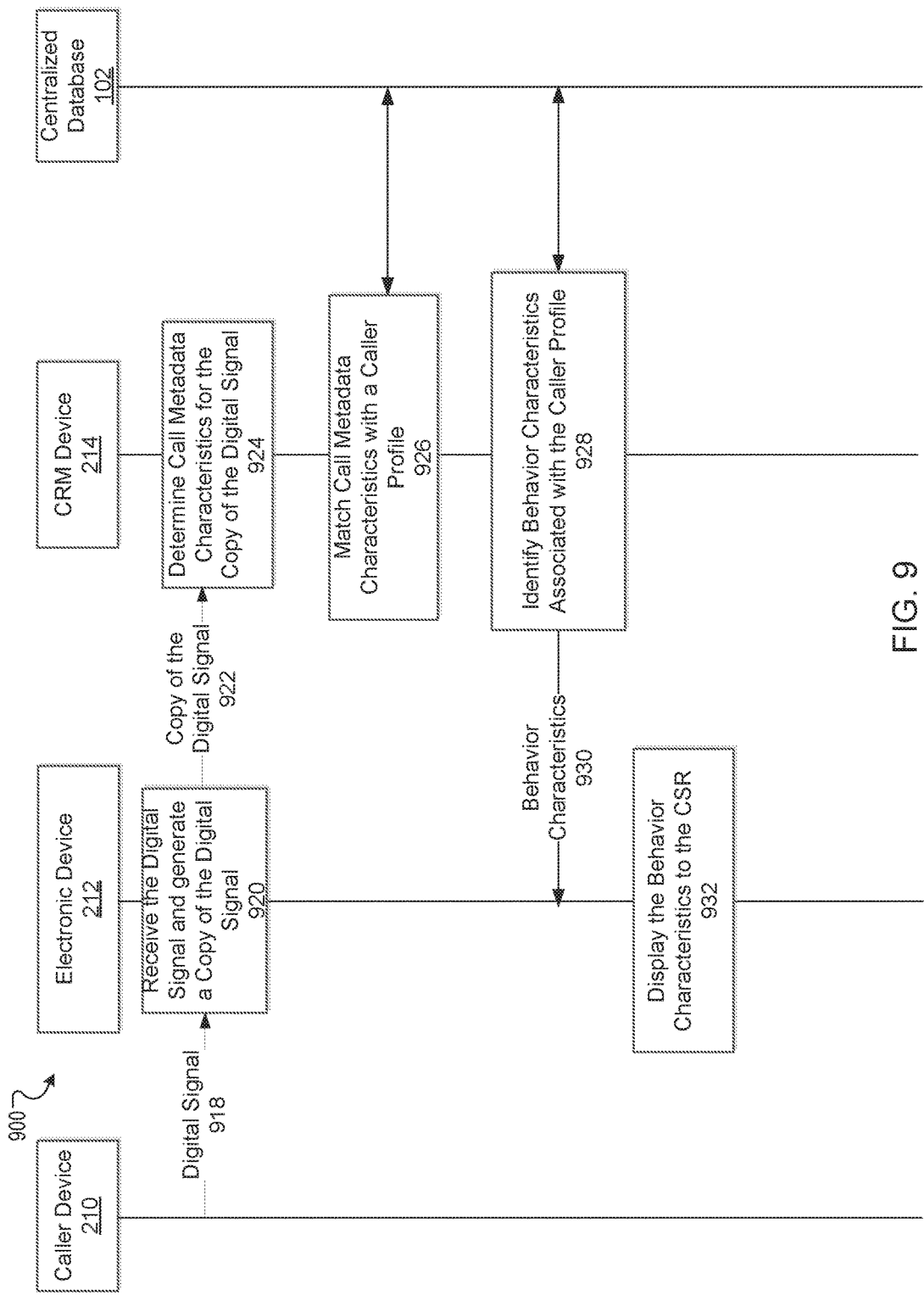
FIG. 9 illustrates a diagram of a method for determining behavior of a caller for different call metadata characteristics according to one embodiment.

FIG. 9 illustrates a diagram of a method 900 for determining behavior of a caller for different call metadata characteristics according to one embodiment. The method 900 may at least partially be performed by processing logic that includes hardware (e.g., circuitry, dedicated logic, programmable logic, microcode, etc.), software (e.g., instructions executed by a processing device), firmware or a combination thereof. The method 900 may be performed by all or part of the CRM device 100 of FIG. 1. For example, the method 900 may be performed by all or part of the processor 110 (FIG. 1) or the communication device 112 (FIG. 1). Some numbers in FIG. 9 are similar to some numbers in FIGS. 1, 2A, and 2B as noted by similar reference numbers unless expressly described otherwise.

Referring to FIG. 9, the method 900 begins with the caller device 210 placing a call to an electronic device 212 (918). The method can include the electronic device 212 receiving a digital signal representative of the call from the caller device 210 and generating a copy of the digital signal (920). The method can include the electronic device 212 sending the copy of the digital signal to the CRM device 214 (922). The method can include the CRM device 214 determining call metadata characteristics for the copy of the call (924). The method can include the CRM device 214 matching call metadata characteristics with a caller profile stored in the centralized database 102 (926). The method can include the CRM device 214 identifying behavior characteristics associated with the caller profile (928).

In one example, the CRM device 100 can use the caller profile to predict a behavior of the caller for different types of calls and/or for different circumstances. In one embodiment, the CRM device 100 tool can compare a caller profile with a call metadata of the current call to predict a behavior of the caller. The caller profile may indicate that the caller previously acted aggressively and hostile when a CSR questions a customer's honesty regarding a product complaint. When the caller calls a call center regarding a buying a product, the CRM device can predict that the caller may again act aggressively and hostile if the CSR questions a customer's honesty.

In one example, the CRM device 100 can determined a caller's voice fingerprint during a first few seconds of a call. The voice fingerprint, separately or in combination with identifying information, can be used to access historical call metadata. In one example, the CRM device 100 can compare the historical call metadata to a current or real-time call with a CSR to determine a change in an emotional state of the caller, such as when the caller may be more or less agitated than during prior calls.

In one embodiment, the CRM device 100 can identify one or more parameters of a caller communication and automatically determines whether the identified parameter of the caller communications indicates a negative or unsatisfactory experience. In one example, the CRM device 100 can identify certain keywords used by a caller to predict a behavior of a caller. For example, a caller can use certain keywords for which many possible synonyms exist. The caller's choice of words that are positive, neutral, or negative can be predictive of the behavior of the caller, such as when the keywords may have been used in previous calls by the caller for similar topics or competing brands. In this example, use of different keywords in relation to different brands can be used to predict a behavior of the caller and/or a caller's preferences.

In another embodiment, a caller may currently be engaged on a call with a CSR of a company selling products for infants. Historical data such as recent prior purchases by the same caller for baby clothes can be predictive that the current call may result in a sale. In another embodiment, the CRM device 100 can determine a predictive score for a sales opportunity based on the historical call metadata. For example, the CRM device 100 can analyze the caller profile to determine that the caller previously responded positively to sales opportunities and typically purchase the product being sold.

In another example, the historical call metadata can indicate that an upset caller had five prior calls that were very positive. The CRM device 100 can determine that a negativity level of a current call may be relevant compared to a baseline positive attitude for the caller, e.g., the negativity may be unique or atypical for the caller. In another example, the historical call metadata can indicate that an upset caller had five prior calls that were very negative or unpleasant. In this example, the CRM device 100 can determine that a negativity level for the current call may not be relevant compared to a baseline negative attitude by the caller, e.g., the negativity may not be unique or atypical for the caller. As discussed in the preceding paragraphs, call metadata from different calls may be aggregated at the central database 102. An advantage of aggregating the different calls can be to enable the CRM device 100 to predict a caller behavior when a particular call event may be a first one experienced by a particular company with a new customer.

In one example, the CRM device 100 can detect a bias of a caller for or against subject matter. For example, the CRM device 100 can perform a psychographic analysis of relative word usage by comparing data from two or more calls to detect bias for or against subject matter. In another example, the CRM device 100 can detect a change or shift in a caller bias by correlating the bias with other criteria, such as a time of a call, events or circumstances surrounding the call, and so forth. In another example, the CRM device 100 can detect a caller bias by identifying a shift in a delta of a call from a baseline for the caller.

In one example, the CRM device 100 can detect a caller preferences and/or caller sensitivity to a brand. For example, the CRM device can use modeling based upon voice analysis of multiple call events, to determine contact preferences for a brand relative to other brands.

The method can include the CRM device 214 sending the behavior characteristics to the electronic device 212 (930). The method can include the electronic device 212 displaying the behavior characteristics to a CSR via a display device of the electronic device 212 (932).

Figure 10:
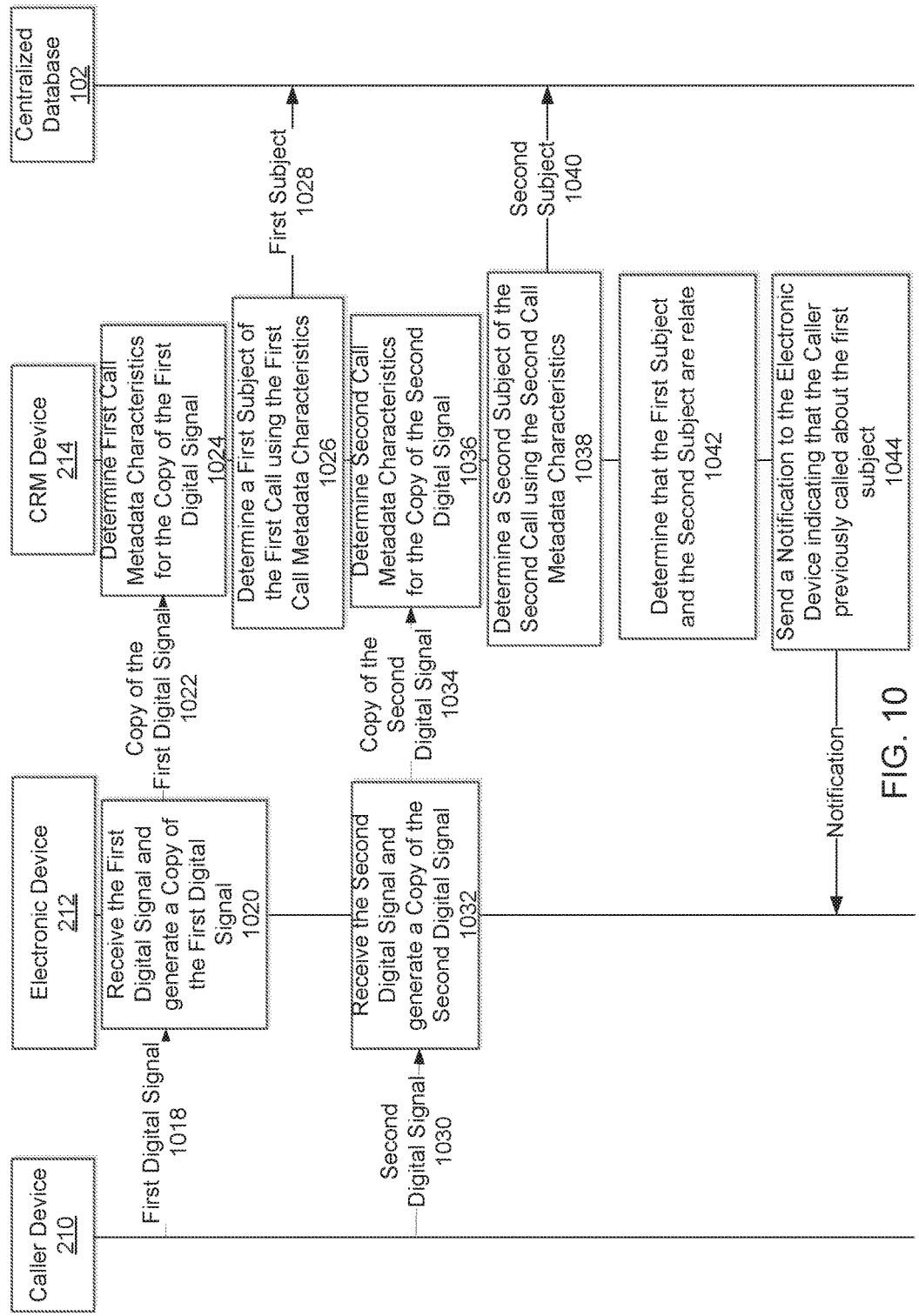
FIG. 10 illustrates a diagram of a method for correlating a first call and a second call from a same caller according to one embodiment.

FIG. 10 illustrates a diagram of a method 1000 for correlating a first call 1018 and a second call 1030 from a same caller according to one embodiment. The method 1000 may at least partially be performed by processing logic that includes hardware (e.g., circuitry, dedicated logic, programmable logic, microcode, etc.), software (e.g., instructions executed by a processing device), firmware or a combination thereof. The method 1000 may be performed by all or part of the CRM device 100 of FIG. 1. For example, the method 1000 may be performed by all or part of the processor 110 (FIG. 1) or the communication device 112 (FIG. 1). Some numbers in FIG. 10 are similar to some numbers in FIGS. 1, 2A, and 2B as noted by similar reference numbers unless expressly described otherwise.

Referring to FIG. 10, the method 1000 begins with the caller device 210 placing a first call to an electronic device 212 (1018). The method can include the electronic device 212 receiving the first digital signal representative of the first call from the caller device 210 and generating a copy of the first digital signal (1020). The method can include the electronic device 212 sending the copy of the first digital signal to the CRM device 214 (1022). The method can include the CRM device 214 determining first call metadata characteristics for the copy of the first digital signal (1024).

The method can include the CRM device 214 determining a first subject of the copy of the first call using the first call metadata characteristics (1026). The method can include the CRM device 214 associating the first subject matter with a caller index ID for the caller and storing the first subject matter in the centralized database 102 (1028). The method can include the caller device 210 placing a second call to an electronic device 212 (1030). The method can include the electronic device 212 receiving a second digital signal representative of the second call from the caller device 210 and generating a copy of the second digital signal (1032). The method can include the electronic device 212 sending the copy of the second digital signal to the CRM device 214 (1034). The method can include the CRM device 214 determining second call metadata characteristics for the copy of the second digital signal (1036). The method can include the CRM device 214 determining a second subject of the copy of the second call using the second call metadata characteristics (1038). The method can include the CRM device 214 associating the second subject matter with a caller index ID for the caller and storing the second subject matter in the centralized database 102 (1040). The method can include the CRM device 214 determining that the first subject and the second subject are related (1042). The method can include the CRM device 214 sending a notification to the electronic device 212, where the notification can indicate that the caller previously called about the first subject (1044).

For example, the CRM device 214 can correlate multiple calls by a caller. In this example, the caller can make a first call to a moving company to get a quote on moving her/his household to Atlanta. Following the first call, the caller can make a second call to another company for a different service offered in the Atlanta area. The CRM device can determine that a voice fingerprint for the caller of the two calls is the same voice fingerprint. The CRM device can further determine that the first call regarding a moving quote may be correlated with the call for the different services. Alternatively, the CRM device can flag the correlated call and indicate to a CSR that the caller may have interest or business in the Atlanta area.

Figure 11:
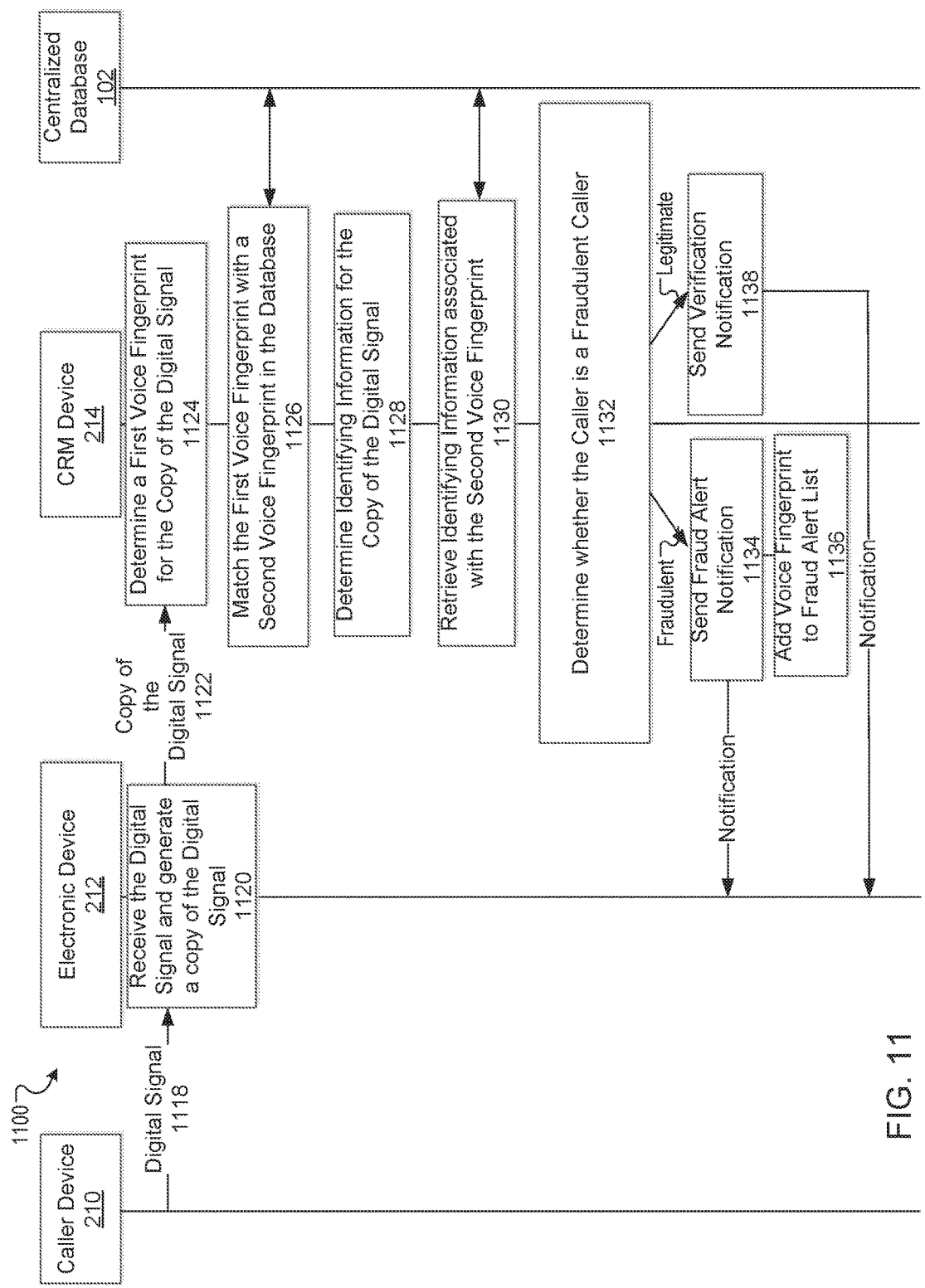
FIG. 11 illustrates a diagram of a method for determining fraudulent behavior of a caller according to one embodiment.

FIG. 11 illustrates a diagram of a method 1100 for determining fraudulent behavior of a caller according to one embodiment. The method 1100 may at least partially be performed by processing logic that includes hardware (e.g., circuitry, dedicated logic, programmable logic, microcode, etc.), software (e.g., instructions executed by a processing device), firmware or a combination thereof. The method 1100 may be performed by all or part of the CRM device 100 of FIG. 1. For example, the method 1100 may be performed by all or part of the processor 110 (FIG. 1) or the communication device 112 (FIG. 1). Some numbers in FIG. 11 are similar to some numbers in FIGS. 1, 2A, and 2B as noted by similar reference numbers unless expressly described otherwise.

To avoid fraud, financial institutions may take a number of steps to accurately identify a caller. A financial institution typically will ask a caller their name, date of birth, address, and other identifying information such as their mother's maiden name. This information, however, may be readily available through internet sources, making it fairly easy for a fraudulent caller to imitate an actual customer. Financial institutions may ask the caller for additional information, such as their last four digits of their social security number, their account numbers, and other identifying information. This additional information provides some enhanced level of security, but can still fall into the wrong hands, resulting in unauthorized access to private accounts. Asking numerous identifying questions also consumes the time of CSRs. Many financial institutions may receive thousands of calls per day. Adding thirty seconds to each call results in significant costs to operate a call center and callers may also become frustrated with having to repeatedly answer identifying questions. While the additional call time result in significant costs, a fraudulent caller may compromise a customer's financial information or other personal information. The compromised financial or other personal information can lead to significant costs to banks, credit cards companies, financial institutions, and other entities that need to authenticate customers.

Referring to FIG. 11, the method 1100 begins with begins with the caller device 210 placing a call to an electronic device 212 (1118). The method can include the electronic device 212 receiving a digital signal representative of the call from the caller device 210 and generating a copy of the digital signal (1120). The method can include the electronic device 212 sending the copy of the digital signal to the CRM device 214 (1122). The method can include the CRM device 214 determining a first voice fingerprint for the copy of the digital signal (1124). The method can include the CRM device 214 matching the first voice fingerprint with a second voice fingerprint in the centralized database 102 (1126). In another example, the CRM device 100 can associate a voice fingerprint with a credit card number and can identify potentially fraudulent activity when a voice fingerprint of a caller using the credit card number does not match the voice fingerprint associated with the credit card number or the voice fingerprint of the caller is unknown. For example, when a caller with an unknown voice fingerprint may be attempting to use a credit card number of a high-value client, the CRM device 100 can identify the activity as potentially fraudulent. In another example, the CRM device 100 can determine that a credit card number may be invalid when the credit card number may not have a voice fingerprint associated with the credit card number.

The method can include the CRM device 214 determining identifying information for the copy of the call (1128). The method can include the CRM device 214 retrieving, from the centralized database 102, identifying information associated with the second voice fingerprint (1130). The method can include determining whether the caller is a fraudulent caller (1132).

In one embodiment, the CRM device 214 can determine that the caller is a fraudulent caller by determining whether there is a mismatch between the identifying information for the copy of the call with the identifying information associated with the second voice fingerprint. In another embodiment, the CRM device 214 can determine that the caller is a fraudulent caller when the caller with a voice fingerprint provides a first name and address during a first call to a financial institution to transfer money. In this example, when the same caller with the same voice fingerprint provides a different name and address during a second call to another financial institution to transfer money, the CRM device 100 can determine the caller may be attempting fraudulent activity.

In another embodiment, the CRM device 100 can prevent false positives when identifying fraudulent activity by correlating the identifying information for the copy of the call with the retrieved identifying information. For example, identifying information from the copy of the call may indicate that a caller may be calling from an area outside of a radius where the caller lives. In this example, the CRM device 100 can confirm an identity of a caller using their voice fingerprint and that the caller activity may be legitimate despite the different in location, such as when the caller may be traveling or on a vacation.

In another embodiment, the identifying information can indicate that the caller may be calling multiple vendors in a same industry, indicating that caller activity may not be fraudulent despite a discrepancy in a voice fingerprint. In another embodiment, the CRM device 100 can determine that a caller with the same voice fingerprint attempted a transaction using two separate credit card numbers, indicating that the activity may be legitimate. In another embodiment, the centralized database 102 may maintain a log of each query or activity associated with a voice fingerprint. In this example, when the caller with the voice fingerprint previously performed the same query or activity as the caller is currently performing, the CRM device 100 can determine the query or activity may be legitimate. Alternatively, when the caller with the voice fingerprint may not have previously performed the same query or activity as the caller is currently performing, the CRM device 100 can determine the query or activity may be fraudulent.

In another embodiment, the CRM device 100 can be used to identify an actual location of a caller when identifying information erroneously identifies a location of the caller. For example, identifying information may indicate that a caller may be located in Texas but each time the caller with the voice fingerprint calls, the location associated with the voice fingerprint may be in Florida.

When the caller is a fraudulent caller performing fraudulent activities, the method can include the CRM device 214 sending a fraud alert notification to the electronic device 212 (1134). The method can include the CRM device 214 adding the voice fingerprint to a fraud alert list (1136). In one example, the CRM device 214 can store the fraud alert list in the centralized database 102. In another example, the CRM device 214 can store the fraud alert list in a memory coupled to the CRM device 214 or integrated into the CRM device 214. In another example, the centralized database 102 can maintain a fraud list of illegitimate callers and their associated voice fingerprints. In this example, when the CRM device 100 identifies an caller on the fraud list may be a current caller talking with a CSR, the CRM device 100 can indicate to a CSR that the call may be fraudulent. When the caller is a legitimate caller performing legitimate activities, the method can include the CRM device 214 sending a verification notification to the electronic device 212 (1140).

Figure 12:
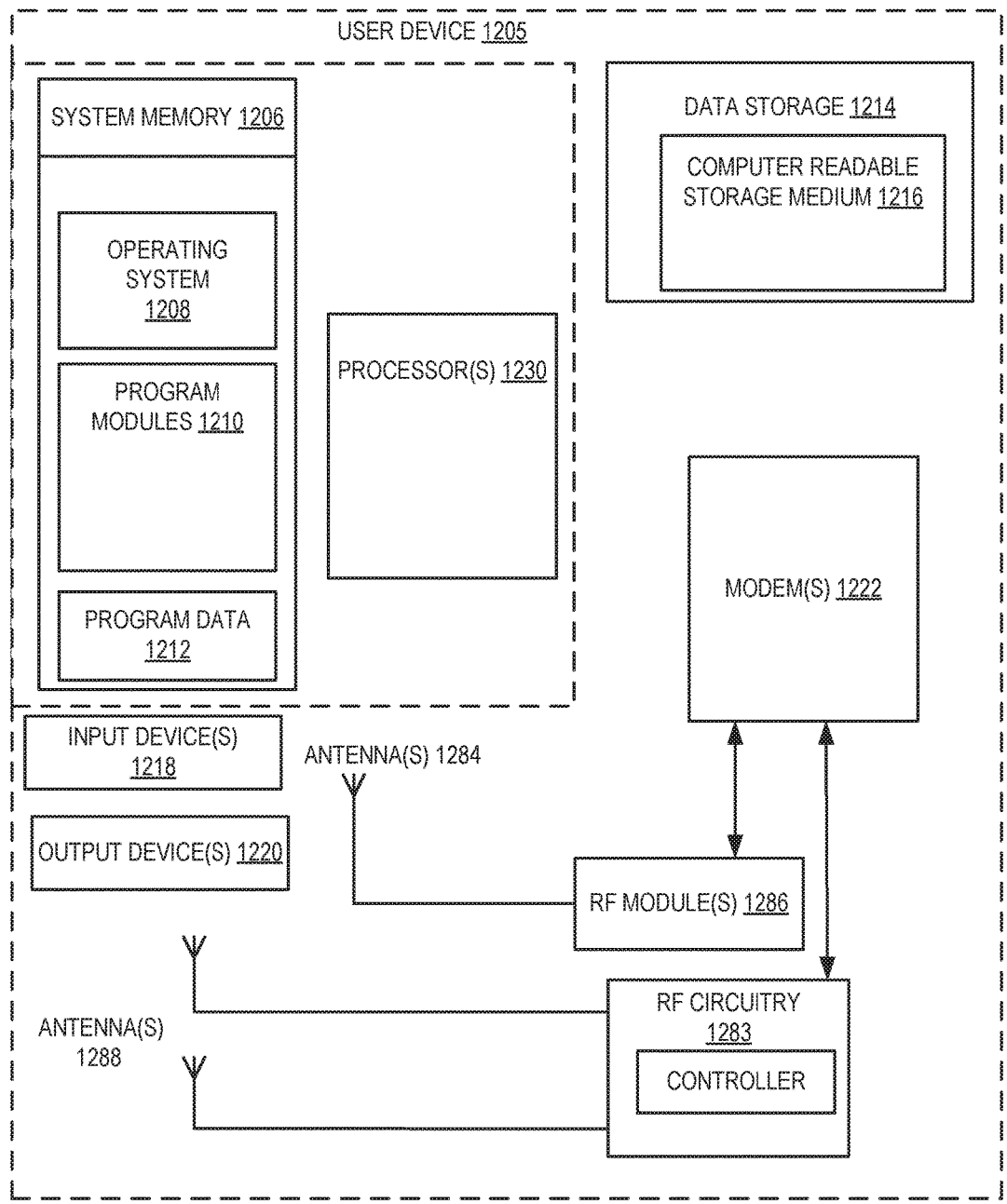
FIG. 12 is a block diagram of a user device in which embodiments of a radio device switching between antennas may be implemented.

FIG. 12 is a block diagram of a user device 1205 in which embodiments of a radio device switching between antennas 1288 may be implemented. The user device 1205 may correspond to the CRM device 100 of FIG. 1 or the CRM device 214 in FIG. 2A. The user device 1205 may be any type of computing device such as an electronic book reader, a PDA, a mobile phone, a laptop computer, a portable media player, a tablet computer, a camera, a video camera, a netbook, a desktop computer, a gaming console, a DVD player, a computing pad, a media center, and the like. The user device 1205 may be any portable or stationary user device. For example, the user device 1205 may be an intelligent voice control and speaker system. Alternatively, the user device 1205 can be any other device used in a WLAN network (e.g., WLAN network), a WAN network, or the like.

The user device 1205 includes one or more processor(s) 1230, such as one or more CPUs, microcontrollers, field programmable gate arrays, or other types of processors. The user device 1205 also includes system memory 1206, which may correspond to any combination of volatile and/or non-volatile storage mechanisms. The system memory 1206 stores information that provides operating system component 1208, various program modules 1210, program data 1212, and/or other components. In one embodiment, the system memory 1206 stores instructions of the methods 200, 300, 400, 500, 600, 700, 800, 900, 1000, and 1100 as described herein. The user device 1205 performs functions by using the processor(s) 1230 to execute instructions provided by the system memory 1206.

The user device 1205 also includes a data storage device 1214 that may be composed of one or more types of removable storage and/or one or more types of non-removable storage. The data storage device 1214 includes a computer-readable storage medium 1216 on which is stored one or more sets of instructions embodying any of the methodologies or functions described herein. Instructions for the program modules 1210 may reside, completely or at least partially, within the computer-readable storage medium 1216, system memory 1206 and/or within the processor(s) 1230 during execution thereof by the user device 1205, the system memory 1206 and the processor(s) 1230 also constituting computer-readable media. The user device 1205 may also include one or more input devices 1218 (keyboard, mouse device, specialized selection keys, etc.) and one or more output devices 1220 (displays, printers, audio output mechanisms, etc.).

The user device 1205 further includes a modem 1222 to allow the user device 1205 to communicate via a wireless network (e.g., such as provided by the wireless communication system) with other computing devices, such as remote computers, an item providing system, and so forth. The modem 1222 can be connected to RF circuitry 1283 and zero or more RF modules 1286. The RF circuit 1283 may include a controller 1285, as described herein. An adaptive neutralization line 160, as described herein is coupled between the antennas 1288 and is coupled to the controller 1283. The RF circuitry 1283 may be a WLAN module, a WAN module, PAN module, or the like. Antennas 1288 are coupled to the RF circuitry 1283, which is coupled to the modem 1222. Zero or more antennas 1284 can be coupled to one or more RF modules 1286, which are also connected to the modem 1222. The zero or more antennas 1284 may be GPS antennas, NFC antennas, other WAN antennas, WLAN or PAN antennas, or the like. The modem 1222 allows the user device 1205 to handle both voice and non-voice communications (such as communications for text messages, multimedia messages, media downloads, web browsing, etc.) with a wireless communication system. The modem 1222 may provide network connectivity using any type of mobile network technology including, for example, cellular digital packet data (CDPD), general packet radio service (GPRS), EDGE, universal mobile telecommunications system (UMTS), 1 times radio transmission technology (1×RTT), evaluation data optimized (EVDO), high-speed down-link packet access (HSDPA), Wi-Fi®, Long Term Evolution (LTE) and LTE Advanced (sometimes generally referred to as 4G), etc.

The modem 1222 may generate signals and send these signals to antenna 1288, and 1284 via RF circuitry 1283 and RF module(s) 1286 as descried herein. User device 1205 may additionally include a WLAN module, a GPS receiver, a PAN transceiver and/or other RF modules. These RF modules may additionally or alternatively be connected to one or more of antennas 1284, 1288. Antennas 1284, 1288 may be configured to transmit in different frequency bands and/or using different wireless communication protocols. The antennas 1284, 1288 may be directional, omnidirectional, or non-directional antennas. In addition to sending data, antennas 1284, 1288 may also receive data, which is sent to appropriate RF modules connected to the antennas.

In one embodiment, the user device 1205 establishes a first connection using a first wireless communication protocol, and a second connection using a different wireless communication protocol. The first wireless connection and second wireless connection may be active concurrently, for example, if a user device is downloading a media item from a server (e.g., via the first connection) and transferring a file to another user device (e.g., via the second connection) at the same time. Alternatively, the two connections may be active concurrently during a handoff between wireless connections to maintain an active session (e.g., for a telephone conversation). Such a handoff may be performed, for example, between a connection to a WLAN hotspot and a connection to a wireless carrier system. In one embodiment, the first wireless connection is associated with a first resonant mode of an antenna structure that operates at a first frequency band and the second wireless connection is associated with a second resonant mode of the antenna structure that operates at a second frequency band. In another embodiment, the first wireless connection is associated with a first antenna element and the second wireless connection is associated with a second antenna element. In other embodiments, the first wireless connection may be associated with a media purchase application (e.g., for downloading electronic books), while the second wireless connection may be associated with a wireless ad hoc network application. Other applications that may be associated with one of the wireless connections include, for example, a game, a telephony application, an Internet browsing application, a file transfer application, a global positioning system (GPS) application, and so forth.

Though a modem 1222 is shown to control transmission and reception via antenna (1284, 1288), the user device 1205 may alternatively include multiple modems, each of which is configured to transmit/receive data via a different antenna and/or wireless transmission protocol.

The user device 1205 delivers and/or receives items, upgrades, and/or other information via the network. For example, the user device 1205 may download or receive items from an item providing system. The item providing system receives various requests, instructions and other data from the user device 1205 via the network. The item providing system may include one or more machines (e.g., one or more server computer systems, routers, gateways, etc.) that have processing and storage capabilities to provide the above functionality. Communication between the item providing system and the user device 1205 may be enabled via any communication infrastructure. One example of such an infrastructure includes a combination of a wide area network (WAN) and wireless infrastructure, which allows a user to use the user device 1205 to purchase items and consume items without being tethered to the item providing system via hardwired links. The wireless infrastructure may be provided by one or multiple wireless communications systems, such as one or more wireless communications systems. One of the wireless communication systems may be a wireless local area network (WLAN) hotspot connected with the network. The WLAN hotspots can be created by products based on IEEE 802.11x standards for the Wi-Fi® technology by Wi-Fi® Alliance. Another of the wireless communication systems may be a wireless carrier system that can be implemented using various data processing equipment, communication towers, etc. Alternatively, or in addition, the wireless carrier system may rely on satellite technology to exchange information with the user device 1205.

The communication infrastructure may also include a communication-enabling system that serves as an intermediary in passing information between the item providing system and the wireless communication system. The communication-enabling system may communicate with the wireless communication system (e.g., a wireless carrier) via a dedicated channel, and may communicate with the item providing system via a non-dedicated communication mechanism, e.g., a public Wide Area Network (WAN) such as the Internet.

The user devices 1205 are variously configured with different functionality to enable consumption of one or more types of media items. The media items may be any type of format of digital content, including, for example, electronic texts (e.g., eBooks, electronic magazines, digital newspapers, etc.), digital audio (e.g., music, audible books, etc.), digital video (e.g., movies, television, short clips, etc.), images (e.g., art, photographs, etc.), and multi-media content. The user devices 1205 may include any type of content rendering devices such as electronic book readers, portable digital assistants, mobile phones, laptop computers, portable media players, tablet computers, cameras, video cameras, netbooks, notebooks, desktop computers, gaming consoles, DVD players, media centers, and the like.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

Embodiments also relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the present invention as described herein. It should also be noted that the terms "when" or the phrase "in response to," as used herein, should be understood to indicate that there may be intervening time, intervening events, or both before the identified operation is performed.

It is to be understood that the above description is intended to be illustrative, and not restrictive. Many other embodiments will be apparent to those of skill in the art upon reading and understanding the above description. The scope of the present embodiments should, therefore, be determined with reference to the appended claims, along with the full scope of equivalents to which such claims are entitled.

Figure 13:
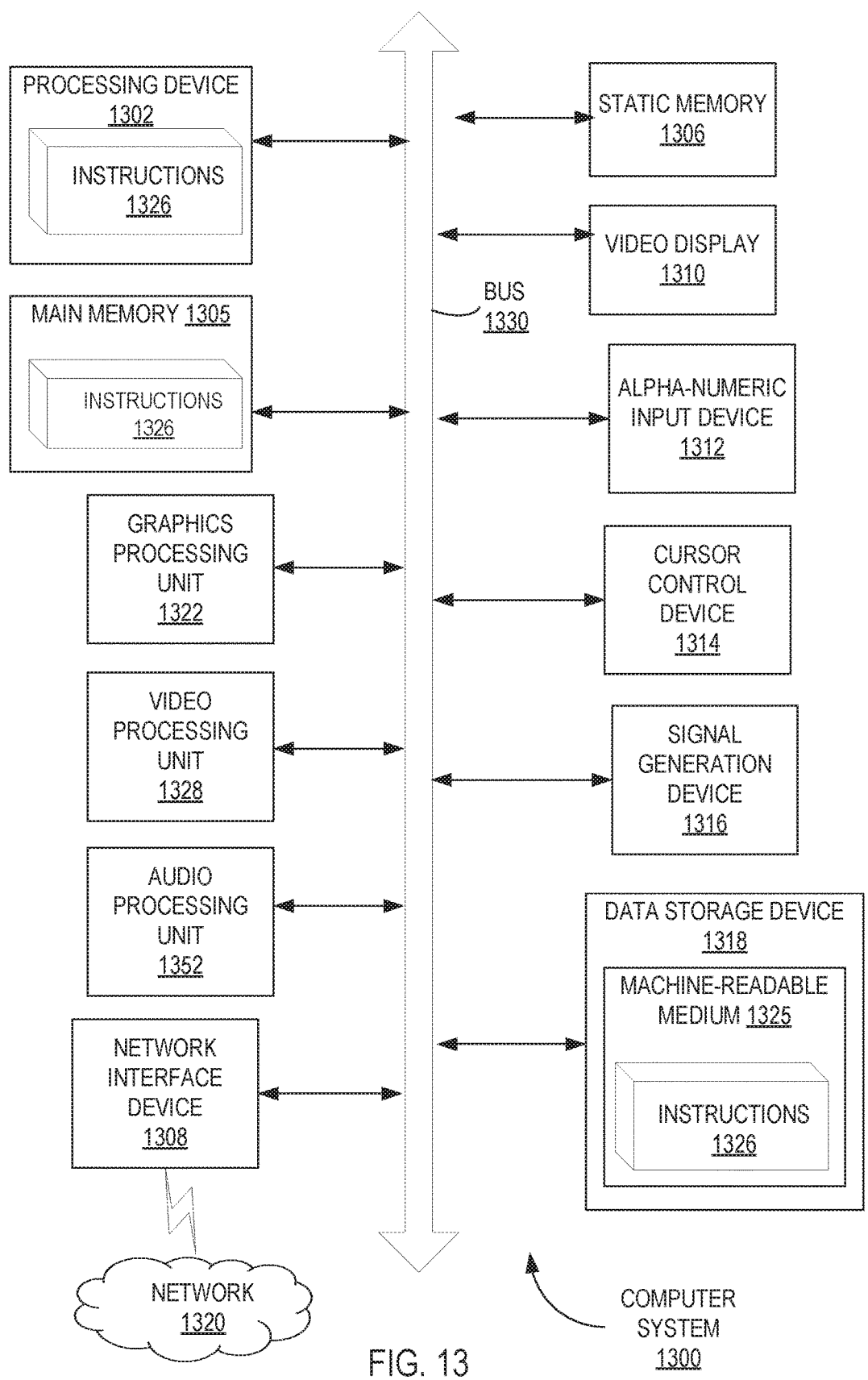
FIG. 13 illustrates a diagrammatic representation of a machine in the example form of a computer system within which a set of instructions, for causing the machine to perform any one or more of the methodologies discussed herein, may be executed.

FIG. 13 illustrates a diagrammatic representation of a machine in the example form of a computer system 1300 within which a set of instructions, for causing the machine to perform any one or more of the methodologies discussed herein, may be executed. In alternative embodiments, the machine may be connected (e.g., networked) to other machines in a LAN, an intranet, an extranet, or the Internet. The machine may operate in the capacity of a server or an electronic device in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a smartphone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1300 may correspond to the CRM device 100 of FIG. 1. The computer system 1300 may correspond to all or part of the CRM device 214 of FIG. 2A.

The computer system 1300 includes: a processing device 1302; a main memory 1304, such as a read-only memory (ROM); flash memory; dynamic random access memory (DRAM), such as synchronous DRAM (SDRAM) or DRAM (RDRAM); a static memory 1306, such as flash memory or static random access memory (SRAM); and a data storage device 1318. The processing device 1302, the main memory 1304, the flash memory, the dynamic random access memory (DRAM), the static memory 1306, and the data storage device 1318 can communicate with each other via a bus 1330.

Processing device 1302 represents one or more processing devices. For example, one or more processing devices can be a microprocessor, central processing unit, or the like. More particularly, the processing device 1302 may be a complex instruction set computing (CISC) microprocessor, a reduced instruction set computer (RISC) microprocessor, a very long instruction word (VLIW) microprocessor, a processor implementing other instruction sets, or a processor implementing a combination of instruction sets. The processing device 1302 may also be one or more special-purpose processing devices. For example, the special-purpose processing devices can be an application specific integrated circuit (ASIC), a field programmable gate array (FPGA), a digital signal processor (DSP), network processor, or the like. In one embodiment, processing device 1302 may include one or more processing cores. The processing device 1302 may be configured to execute the instructions 1326 of a mirroring logic stored in the main memory 1305 for performing the operations discussed herein.

The computer system 1300 may further include a network interface device 1308 communicably coupled to a network 1320. The computer system 1300 also may include: a video display unit 1310, such as a liquid crystal display (LCD) or a cathode ray tube (CRT); an alphanumeric input device 1312, such as a keyboard; a cursor control device 1314, such as a mouse; a signal generation device 1316, such as a speaker; or other peripheral devices. Furthermore, the computer system 1300 may include a graphics processing unit 1322, a video processing unit 1328, and an audio processing unit 1332. In another embodiment, the computer system 1300 may include a chipset, which refers to a group of integrated circuits, or chips, that is designed to work with the processing device 1302. The chipset may control communications between the processing device 1302 and external devices. For example, the chipset may be a set of chips on a motherboard that links the processing device 1302 to high-speed devices, such as main memory 1304 and graphic controllers, as well as linking the processing device 1302 to lower-speed peripheral buses of peripherals, such as a universal serial bus (USB), a peripheral component interconnect (PCI), or industry standard architecture (ISA) buses.

The data storage device 1318 may include a computer-readable storage medium 1325 that stores instructions 1326. The instructions 1326 may embody any one or more of the methodologies of functions described herein. The instructions 1326 may also reside, completely or at least partially, within the main memory 1304 and/or within the processing device 1302 during execution thereof by the computer system 1300. The main memory 1304 and the processing device 1302 may be computer-readable storage media.

The computer-readable storage medium 1324 may store instructions 1326 utilizing logic and/or a software library containing methods that call the above applications. While the computer-readable storage medium 1324 is shown in an example embodiment to be a single medium, the term "computer-readable storage medium" or "computer-readable medium" is not intended to be limiting. The "computer-readable storage medium" or "computer-readable medium" can be a single medium or multiple media, such as a centralized or distributed database, and/or associated caches and servers, that store the one or more sets of instructions. The term "computer-readable storage medium" can include any medium that is capable of storing, encoding or carrying a set of instruction for execution by the machine and that cause the machine to perform any one or more of the methodologies of the present embodiments. The term "computer-readable storage medium" can include, but not be limited to, solid-state memories, optical media, and magnetic media.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

Although the embodiments may be herein described with reference to specific integrated circuits, such as in computing platforms or microprocessors, other embodiments are applicable to other types of integrated circuits and logic devices. Similar techniques and teachings of embodiments described herein may be applied to other types of circuits or semiconductor devices. For example, the disclosed embodiments are not limited to desktop computer systems or laptops and may also be used in other devices, such as handheld devices, tablets, other thin notebooks, systems on a chip (SOC) devices, and embedded applications. Some examples of handheld devices include cellular phones, Internet protocol (IP) devices, smartphones, digital cameras, personal digital assistants (PDAs), and handheld personal computers (PCs). Embedded applications can include microcontrollers, digital signal processors (DSPs), SoCs, network computers (NetPC), set-top boxes, network hubs, wide area network (WAN) switches, or other systems that may perform the functions and operations, as discussed in the proceeding paragraphs.

Although the embodiments described herein may refer to a processor or processing device, other embodiments are applicable to other types of integrated circuits and logic devices. Similar techniques and teachings of embodiments may be applied to other types of circuits or semiconductor devices that may benefit from higher pipeline throughput and improved performance. The embodiments herein are applicable to any processor or machine that performs data manipulations. However, the embodiments are not limited to processors or machines that perform 512 bit, 256 bit, 128 bit, 64 bit, 32 bit, and/or 16 bit data operations and may be applied to any processor and machine in which manipulation or management of data is performed.

The embodiments herein provide examples, and the accompanying drawings show various examples for the purposes of illustration. However, these examples should not be construed to be limiting, as they are merely intended to provide examples of embodiments rather than to provide an exhaustive list of all possible implementations of embodiments.

Some portions of the detailed description are presented in terms of algorithms and symbolic representations of operations on data bits within a computer memory. These algorithmic descriptions and representations are used by those skilled in the data processing arts to most effectively convey the substance of their work to others skilled in the art. An algorithm is here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. The blocks described herein may be hardware, software, firmware, or a combination thereof.

The terms in the preceding paragraphs and similar terms are to be associated with the appropriate physical quantities and are merely convenient labels applied to these quantities. Unless specifically stated otherwise as apparent from the preceding paragraphs and figures, discussions utilizing terms such as "detecting," "initiating," "determining," "continuing," "halting," "receiving," "recording," or the like, refer to the actions and processes of a computing system, or similar electronic computing device, that manipulates and transforms data represented as physical (e.g., electronic) quantities within the computing system registers and memories into other data similarly represented as physical quantities within the computing system memories, computer system registers, other information storage devices, other transmission devices, or electronic devices.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," etc. as used herein are meant as labels to distinguish among different elements and may not necessarily have an ordinal meaning according to their numerical designation.

Embodiments described herein may also relate to an apparatus for performing the operations herein. This apparatus may be specially constructed for the required purposes, or it may comprise a computer selectively activated or reconfigured by a computer program stored in the computer. Such a computer program may be stored in a non-transitory computer-readable storage medium, such as, but not limited to, any type of disk including floppy disks, optical disks, CD-ROMs and magnetic-optical disks, read-only memories (ROMs), random access memories (RAMs), erasable programmable read only memories (EPROMs), electrically erasable programmable read only memories (EEPROMs), magnetic or optical cards, flash memory, or any type of media suitable for storing electronic instructions. The term "computer-readable storage medium" can include a single medium or multiple mediums that store the one or more sets of instructions. The single medium or multiple mediums can be centralized or distributed databases and/or associated caches and servers. The term "computer-readable medium" can include any medium that is capable of storing, encoding or carrying a set of instructions for execution by the machine and that causes the machine to perform any one or more of the methodologies of the embodiments herein. The term "computer-readable storage medium" can include, but not be limited to, solid-state memories, optical media, magnetic media, or any medium that is capable of storing a set of instructions for execution by the machine and that causes the machine to perform any one or more of the methodologies of the embodiments herein.

The algorithms and displays presented herein are not inherently related to any particular computer or other apparatus. Various computing systems may be used with programs in accordance with the teachings herein, or it may prove convenient to construct a more specialized apparatus to perform the operations. The required structure for a variety of these systems will appear from the description in the proceeding paragraphs. In addition, the embodiments herein are not described with reference to any particular programming language. It will be appreciated that a variety of programming languages may be used to implement the teachings of the embodiments herein.

The preceding description sets forth numerous specific details such as examples of specific systems, components, methods and so forth, in order to provide a good understanding of several embodiments. It will be apparent to one skilled in the art, however, that at least some embodiments may be practiced without these specific details. In other instances, well-known components or methods are not described in detail or are presented in simple block diagram format in order to avoid unnecessarily obscuring the embodiments herein. Thus, the specific details set forth above are merely exemplary. Particular implementations may vary from these exemplary details and still be contemplated to be within the scope of the present embodiments.

The preceding description is illustrative and not restrictive. Many other embodiments will be apparent to those of skill in the art upon reading and understanding the preceding description. The scope of the embodiments herein should be determined with reference to the appended claims, along with the full scope of equivalents to which such claims are entitled.

What is claimed is:

1. A customer relationship management (CRM) device comprising:
    a memory to store instructions;
    a network interface coupled to a first call monitoring system and a second call monitoring system, wherein:
        the first call monitoring system is coupled to a first electronic device, and
        the second call monitoring system is coupled to a second electronic device;
    a database interconnect coupling a processor to a centralized database; and
    the processor coupled to the memory, wherein when the processor executes the instructions the processor is to:
        receive, from the first call monitoring system via the network interface, a copy of a first digital audio signal in response to the first electronic device receiving the first digital audio signal, wherein the first digital audio signal is representation of a first call between the first electronic device and a caller device;
        processing the copy of the first digital signal to generate first call metadata, wherein the first call metadata comprises a voice fingerprint for the caller;
        determine that the centralized database is not storing any entries with the voice fingerprint for the caller;
        generate a caller index identifier (ID) and a caller profile for the caller, wherein the caller index ID and the caller profile is anonymized;
        add the first call metadata to the caller profile;
        store the caller profile and the caller index ID in an entry of the centralized database;
        receive, from the second call monitoring system via the network interface, a copy of a second digital audio signal in response to the second electronic device receiving the second digital audio signal, wherein the second digital audio signal is representation of a second call between the second electronic device and the caller device;
        processing the second digital signal to determine second call metadata, wherein the second call metadata comprises the voice fingerprint for the caller;
        add the second call metadata to the caller profile;
        determine that the entry is not storing a threshold amount of call metadata to determine a complete caller profile; and
        operate in a training mode to collect additional call metadata to update the caller profile with additional call metadata.

2. The CRM device of claim 1, wherein the processor is further to:
    determine one or more call metadata characteristics for the second call metadata;
    determine that the one or more call metadata characteristics meet a threshold quality level; and
    update the caller profile with the second call metadata.

3. The CRM device of claim 1, wherein the processor is further to:
    determine one or more call metadata characteristics for the second call metadata;
    determine that the one or more call metadata characteristics do not meet a threshold quality level; and
    disregard the second call metadata.

4. The CRM device of claim 1, wherein:
    the first electronic device is a first communication system for telephonic communications,
    the first electronic device is located at a first call agent location,
    the second electronic device is a second communication system for telephonic communications, and
    the second electronic device is located at a second call agent location.

5. The CRM device of claim 1, wherein the processor is further to:
    determine one or more call metadata characteristics for the second call metadata;
    determine that the one or more call metadata characteristics do not meet a threshold quality level; and
    perform secondary verification of the call metadata.

6. The CRM device of claim 5, wherein the one or more call metadata characteristics comprises call quality information, a volume level of the call, an audio quality level of the call, a video quality level of the call, a length of time of the call, call content, key words used during the call, a speed of speech of the caller, speech pattern information, grammar usage, or voice identification information.

7. The CRM device of claim 1, wherein the processor is further to:
    determine that the caller is a first-time caller;
    determine one or more call metadata characteristics for the call metadata;
    identify a second caller profile for a second caller that comprises one or more call metadata characteristics that match the one or more call metadata characteristics for the call metadata;
    associate the second caller profile with the caller index ID of the first-time caller; and
    send the second caller profile to the second electronic device.

8. A customer relationship management (CRM) device comprising:
    a memory to store instructions;
    a network interface coupled to a call monitoring system, wherein the call monitoring system is coupled to an electronic device, and
    a database interconnect coupling a processor to a centralized database; and
    the processor coupled to the memory, wherein when the processor executes the instructions the processor is to:

receive, from the call monitoring system via the network interface, a copy of a digital audio signal in response to the electronic device receiving the digital audio signal, wherein the digital audio signal is representation of a call between the electronic device and a caller device;

process the copy of the digital signal to generate call metadata, wherein the call metadata comprises a voice fingerprint for the caller;

determine that the centralized database is storing an entry with the voice fingerprint associated with the caller;

add the call metadata to a caller profile stored in the entry of the centralized database;

determine that the centralized database is storing a threshold amount of call metadata to determine a personality type of a caller associated with the call metadata; and switch from operating in a training mode to operating in an active mode for the caller profile.

9. The CRM device of claim 8, wherein the processor is to determine the personality type of the caller using by matching the call metadata with predefined metadata for a personality type of a psychological behavioral model.

10. The CRM device of claim 8, wherein the processing device is further to:

identify behavior characteristic information associated with the caller profile; and send the behavior characteristic information to the electronic device.

11. The CRM device of claim 8, further comprising:

a second call monitoring system is coupled to a second electronic device and the network interface;

wherein the processor is further to:

determine a first call metadata characteristic for the call metadata;

determine a first subject of the call using the call metadata characteristic;

receive, from the second call monitoring system via the network interface, a second copy of a second digital audio signal in response to the second electronic device receiving the second digital audio signal, wherein the second digital audio signal is representation of a second call between the second electronic device and the caller device;

process the second copy of the digital signal to determine second call metadata, wherein the second call metadata comprises the voice fingerprint for the caller;

determine second call metadata characteristic for the second call metadata;

determine a second subject of the second call using the second call metadata characteristic; and send a notification to the second electronic device indicating that the caller previously called about the first subject.

12. The CRM device of claim 8, wherein network connection is a cellular communication channel or a wireless local area network (WLAN) communication channel.

13. The CRM device of claim 8, wherein the centralized database stores call metadata for a plurality of digital audio signals from a plurality of call monitoring systems for a plurality of call agents.

14. A non-transitory machine-readable storage medium having instructions that, when executed by a processing device, cause the processing device to perform operations comprising:

retrieving, from a centralized database, call metadata associated with a caller index identifier (ID) of a caller;

determining call metadata characteristics for the call metadata;

match the call metadata characteristics of the call metadata with characteristics associated with a personality type of a psychological behavioral model;

generating a caller profile that comprises personality type information for the personality type;

associating the caller profile with the caller index ID; and storing the caller profile in an entry in the centralized database associated with the caller index ID.

15. The non-transitory machine-readable storage medium of claim 14, wherein the personality type comprises a reactor, a workaholic, a persister, a dreamer, a rebel, a promoter, an extravert, an introvert, a mechanic, an analytical, a nurturer, a generous person, or a selfish person.

16. The non-transitory machine-readable storage medium of claim 14, wherein the processing device is further to perform operations comprising determining the personality type of the caller by matching call metadata characteristics with predetermined personality characteristics associated with the psychological behavioral model, the predetermined personality characteristics comprising a length of the call by the caller, a tone of voice of the caller used during the call, keywords used by the caller during the call, a speed of the caller's speech, a frequency of keywords used by the caller during the call, and so forth.

17. The non-transitory machine-readable storage medium of claim 14, wherein the processing device is further to determine the personality type of the caller by comparing caller responses to predictive questions in the call with predetermined answers for the predictive questions.

18. The non-transitory machine-readable storage medium of claim 14, wherein the processing device is further to perform operations comprising:

receiving, from an electronic device, a digital audio signal representative of a copy of a call between the electronic device and a caller device;

identifying the caller profile for the caller by matching call metadata characteristics for the digital audio signal with the call metadata characteristics of the retrieved call metadata; and sending the caller profile to the electronic device.

19. The non-transitory machine-readable storage medium of claim 18, wherein the processing device to perform operations comprising:

anonymizing the caller profile to remove personal data from the caller profile;

processing the call metadata to determine a first voice fingerprint for the caller, wherein the voice fingerprint does not include personal data from the caller; and identifying the caller profile for the caller by matching the voice fingerprint with a second voice fingerprint stored in the centralized database.

20. The non-transitory machine-readable storage medium of claim 14, wherein the processing device is further to perform operations comprising:

receiving, from a call monitoring system, a copy of a digital audio signal, wherein the digital audio signal is representation of a call between an electronic device and a caller device;

processing the copy of the digital signal to determine call metadata, wherein the call metadata comprises identifying information of a caller or a voice fingerprint for the caller;

determining that characteristics of the call metadata do not match with the characteristics of the retrieved call metadata; and sending, to the electronic device, a notification that a behavior of the caller is deviating from the caller profile in response to the call metadata not matching with the characteristics of the retrieved call metadata.

\* \* \* \* \*